(12) United States Patent
Bornhoevd et al.

(10) Patent No.: US 11,046,732 B2
(45) Date of Patent: Jun. 29, 2021

(54) MICROORGANISM STRAIN AND METHOD FOR ANTIBIOTIC-FREE, FERMENTATIVE PREPARATION OF LOW MOLECULAR WEIGHT SUBSTANCES AND PROTEINS

(71) Applicant: WACKER CHEMIE AG, Munich (DE)

(72) Inventors: Carsten Bornhoevd, Munich (DE); Marcel Thoen, Halle (DE)

(73) Assignee: WACKER CHEMIE AG, Munich (DE)

( * ) Notice: Subject to any disclaimer, the term of this patent is extended or adjusted under 35 U.S.C. 154(b) by 459 days.

(21) Appl. No.: 15/779,773

(22) PCT Filed: Dec. 11, 2015

(86) PCT No.: PCT/EP2015/079488
§ 371 (c)(1),
(2) Date: May 29, 2018

(87) PCT Pub. No.: WO2017/097383
PCT Pub. Date: Jun. 15, 2017

(65) Prior Publication Data
US 2019/0284245 A1 Sep. 19, 2019

(51) Int. Cl.

| | |
|---|---|
| C07K 14/195 | (2006.01) |
| C12P 21/02 | (2006.01) |
| C12N 15/74 | (2006.01) |
| C12N 9/10 | (2006.01) |
| C12P 13/12 | (2006.01) |
| C07K 16/00 | (2006.01) |
| C07K 16/40 | (2006.01) |
| C12N 9/12 | (2006.01) |
| C12N 15/70 | (2006.01) |
| C07K 14/245 | (2006.01) |
| C12N 1/04 | (2006.01) |
| C12N 1/38 | (2006.01) |
| C12N 15/63 | (2006.01) |
| C12N 1/20 | (2006.01) |

(52) U.S. Cl.
CPC .......... *C07K 14/195* (2013.01); *C07K 14/245* (2013.01); *C07K 16/00* (2013.01); *C07K 16/40* (2013.01); *C12N 1/04* (2013.01); *C12N 1/20* (2013.01); *C12N 1/38* (2013.01); *C12N 9/1029* (2013.01); *C12N 9/1074* (2013.01); *C12N 9/1205* (2013.01); *C12N 15/63* (2013.01); *C12N 15/70* (2013.01); *C12N 15/74* (2013.01); *C12P 13/12* (2013.01); *C12P 21/02* (2013.01); *C07K 2317/55* (2013.01); *C12N 2510/02* (2013.01)

(58) Field of Classification Search
None
See application file for complete search history.

(56) References Cited

U.S. PATENT DOCUMENTS

| | | | |
|---|---|---|---|
| 5,972,663 | A | 10/1999 | Winterhalter et al. |
| 2008/0076157 | A1 | 3/2008 | Leonhartsberger et al. |
| 2008/0076158 | A1 | 3/2008 | Dassler et al. |
| 2008/0254511 | A1 | 10/2008 | Dassler et al. |
| 2010/0248306 | A1 | 9/2010 | Cadot et al. |

FOREIGN PATENT DOCUMENTS

| | | |
|---|---|---|
| EP | 0185512 A1 | 6/1986 |
| EP | 0251579 A1 | 1/1988 |
| EP | 0284126 A1 | 9/1988 |
| EP | 0885962 A1 | 12/1998 |
| WO | 2007039632 A1 | 4/2007 |
| WO | 2008135113 A1 | 11/2008 |
| WO | 2016073079 A2 | 5/2016 |

OTHER PUBLICATIONS

Aseev et al., "A new regulatory circuit in ribosomal protein operons: S2-mediated control of the rpsB-tsf expression in vivo", RNA, vol. 14(9), p. 1882-94 (2008).
Baba et al., "Construction of *Escherichia coli* K-12 in-frame, single-gene knockout mutants: the Keio collection", Molecular systems biology, vol. 2, p. 1-169, with Supplementary Tables 6 and 7 and Legend to Supplementary Figures and Tables (2006).
Bron et al., "Segregational instability of pUB110-derived recombinant plasmids in Bacillus subtilis" Plasmid, vol. 14(3), p. 235-44 (1985).
Bucurenci et al., "Mutational Analysis of UMP Kinase from *Escherichia coli*", Journal of bacteriology, vol. 180(3), p. 473-7 (1998).
Chang et al., "Methionine aminopeptidase gene of *Escherichia coli* is essential for cell growth", Journal of bacteriology, vol. 171(7), p. 4071-2 (1989).
Choi et al., "Secretory and extracellular production of recombinant proteins using *Escherichia coli*", Applied microbiology and biotechnology, vol. 64(5), p. 625-35 (2004).
Coleman "Characterization of *Escherichia coli* cells deficient in 1-acyl-sn-glycerol-3-phosphate acyltransferase activity", Journal of Biological Chemistry, vol. 265(28), p. 17215-21 (1990).
Datsenko et al., "One-step inactivation of chromosomal genes in *Escherichia coli* K-12 using PCR products", Proceedings of the National Academy of Sciences, vol. 97(12), p. 6640-5 (2000).
Guzman et al., "FtsL, an essential cytoplasmic membrane protein involved in cell division in *Escherichia coli*", Journal of bacteriology, vol. 174(23), p. 7717-28 (1992).

(Continued)

*Primary Examiner* — Suzanne M Noakes
(74) *Attorney, Agent, or Firm* — Caesar Rivise, PC

(57) ABSTRACT

The invention relates to a microorganism strain and a method for antibiotic-free fermentative preparation of low molecular weight substances and proteins. The microorganism strain for producing low molecular weight substances or proteins contains in its genome a mutation in a gene which brings about an auxotrophy in the strain. It further contains a production plasmid coding an enzyme for production of a low molecular weight substance or a recombinant protein and a functional copy of the gene whose chromosomal inactivation brings about the auxotrophy, wherein the auxotrophy is a non-feedable auxotrophy.

8 Claims, 19 Drawing Sheets

Specification includes a Sequence Listing.

(56) References Cited

OTHER PUBLICATIONS

Hagg et al., "A host/plasmid system that is not dependent on antibiotics and antibiotic resistance genes for stable plasmid maintenance in *Escherichia coli*", Journal of biotechnology, vol. 111(1), p. 17-30 (2004).

Sakamoto et al., "Structure—function relationships of UMP kinases from pyrH mutants of Gram-negative bacteria", Microbiology, vol. 150(7), p. 2153-9 (2004).

Sodoyer et al., "Antibiotic-Free Selection for Bio-Production: Moving Towards a New 'Gold Standard'", In Antibiotic Resistant Bacteria—A Continuous Challenge in the New Millennium, InTech, (2012).

Gaitonde, "A spectrophotometric method for the direct determination of cysteine in the presence of other naturally occurring amino acids", Biochemical Journal, vol. 104(2), p. 627-33 (1967).

Gerdes et al., "Unique type of plasmid maintenance function: postsegregational killing of plasmid-free cells", Proceedings of the National Academy of Sciences, vol. 83(10), p. 3116-20 (1986).

Hashimoto-Gotoh et al., "A set of temperature sensitive-replication/-segregation and temperature resistant plasmid vectors with different copy numbers and in an isogenic background (chloramphenicol, kanamycin, lacZ, repA, par, polA)", Gene, vol. 241(1), p. 185-91 (2000).

Herrero et al., "Transposon vectors containing non-antibiotic resistance selection markers for cloning and stable chromosomal insertion of foreign genes in gram-negative bacteria", Journal of bacteriology, vol. 172(11), p. 6557-67 (1990).

Link et al., "Methods for generating precise deletions and insertions in the genome of wild-type *Escherichia coli*: application to open reading frame characterization", Journal of bacteriology, vol. 179(20), p. 6228-37 (1997).

Morand et al., "Alteration of the fatty acid substrate specificity of lysophosphatidate acyltransferase by site-directed mutagenesis", Biochemical and biophysical research communications, vol. 244(1), p. 79-84 (1998).

Peubez et al., "Antibiotic-free selection in *E. coli*: new considerations for optimal design and improved production", Microbial cell factories, vol. 9(1), p. 65 (2010).

Shokri et al., "Cell and process design for targeting of recombinant protein into the culture medium of *Escherichia coli*", Applied microbiology and biotechnology, vol. 60(6), p. 654-64 (2003).

Skerra, "A general vector, pASK84, for cloning, bacterial production, and single-step purification of antibody Fab fragments", Gene, vol. 141(1), p. 79-84 (1994).

International Preliminary Report on Patentability of PCT/EP2015/079488 (dated Feb. 15, 2018).

International Search Report of PCT/EP2015/079488 (dated May 23, 2016).

Zhang et al. Advances of Red Recombination System in *Escherichia coli* Gene Modification. China Biotechnology, vol. 28, No. 12, published on Dec. 31, 2008 with English Abstract.

Fig. 1: pKD46
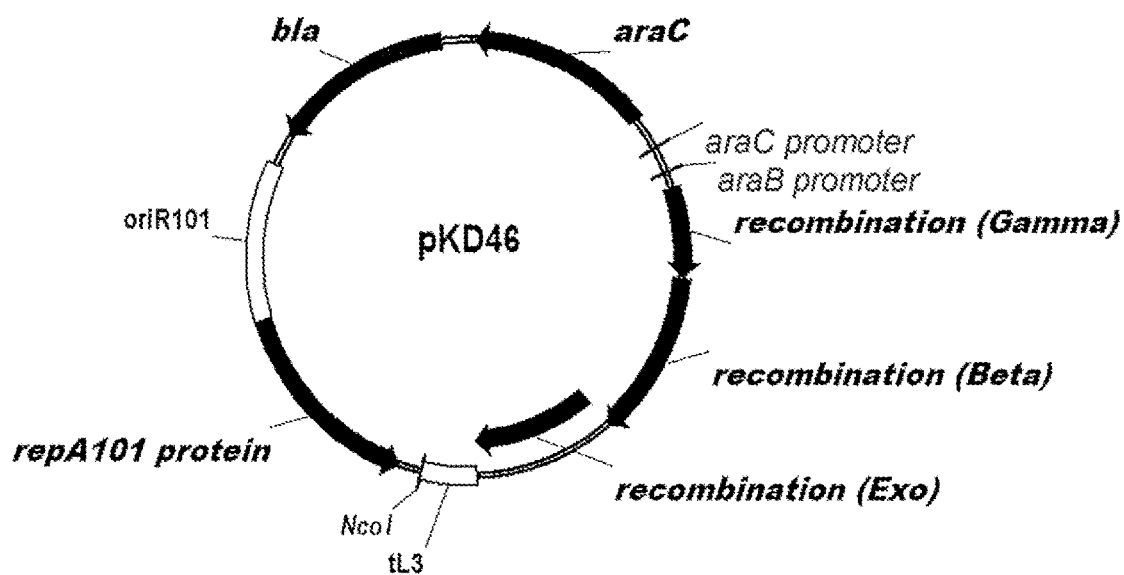

Fig. 2: pAF-ts-pyrH
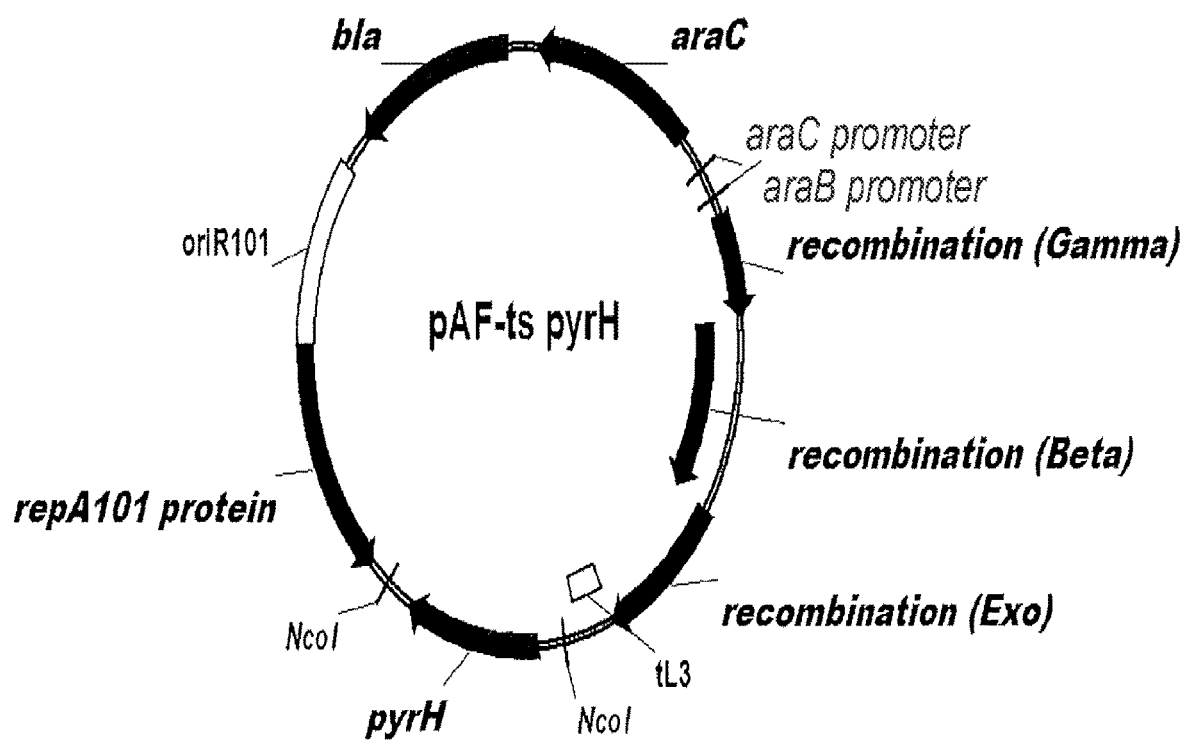

Fig. 3: pAF-ts-plsC
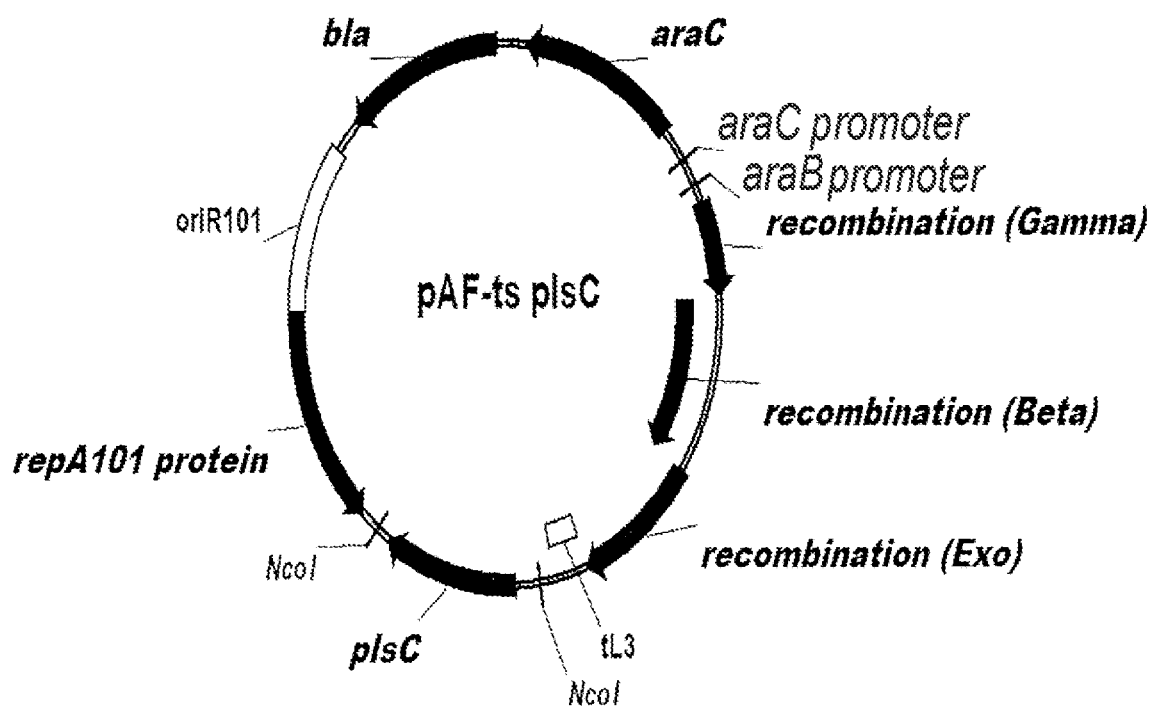

Fig. 4: pMT1
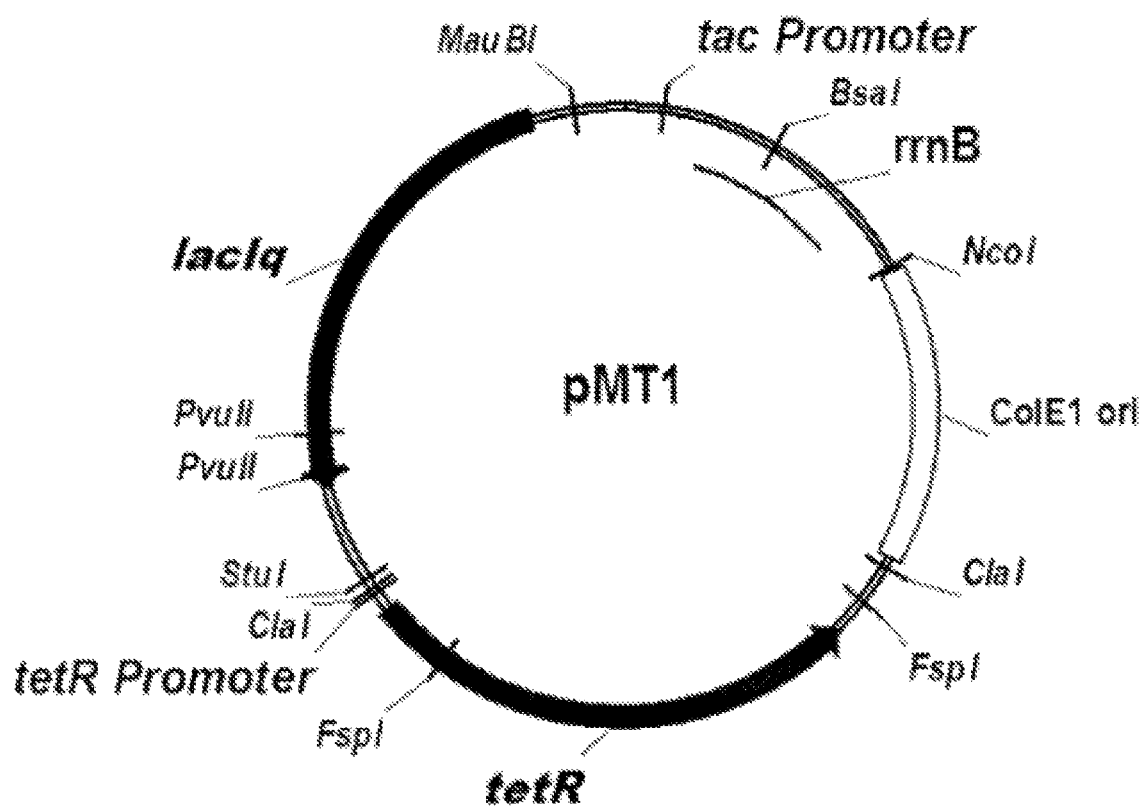

Fig. 5: pcysEX-GAPDH-ORF306_tetR
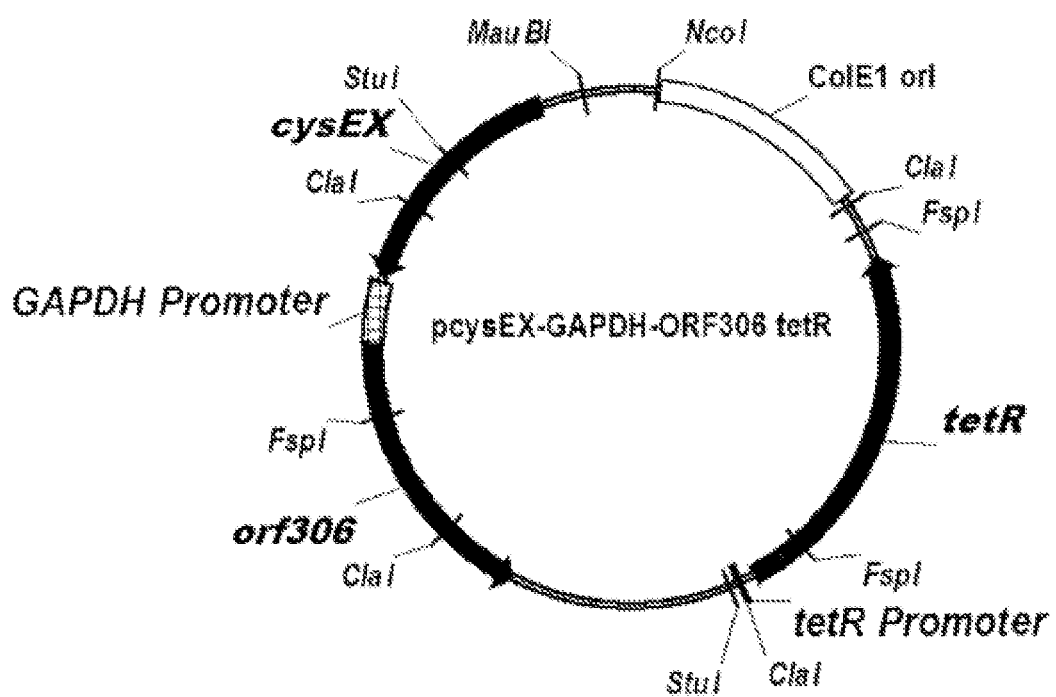

Fig. 6: pCGT_tetR
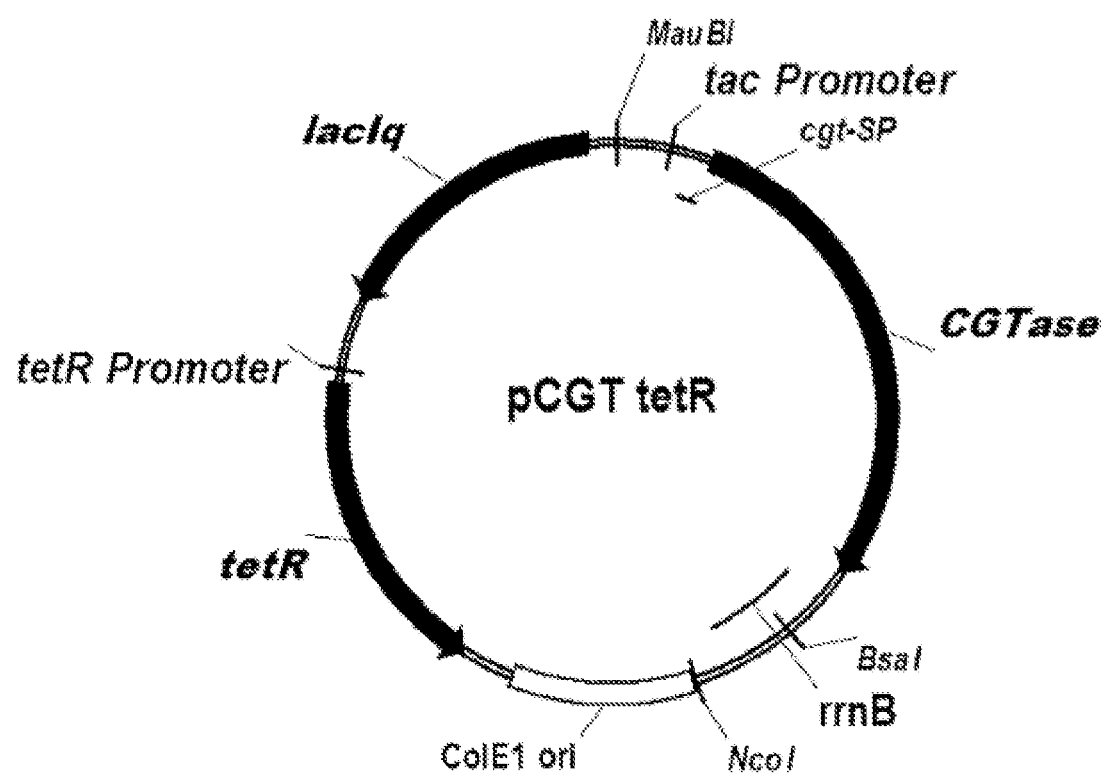

Fig. 7: pFab-anti-Lysozyme_tetR
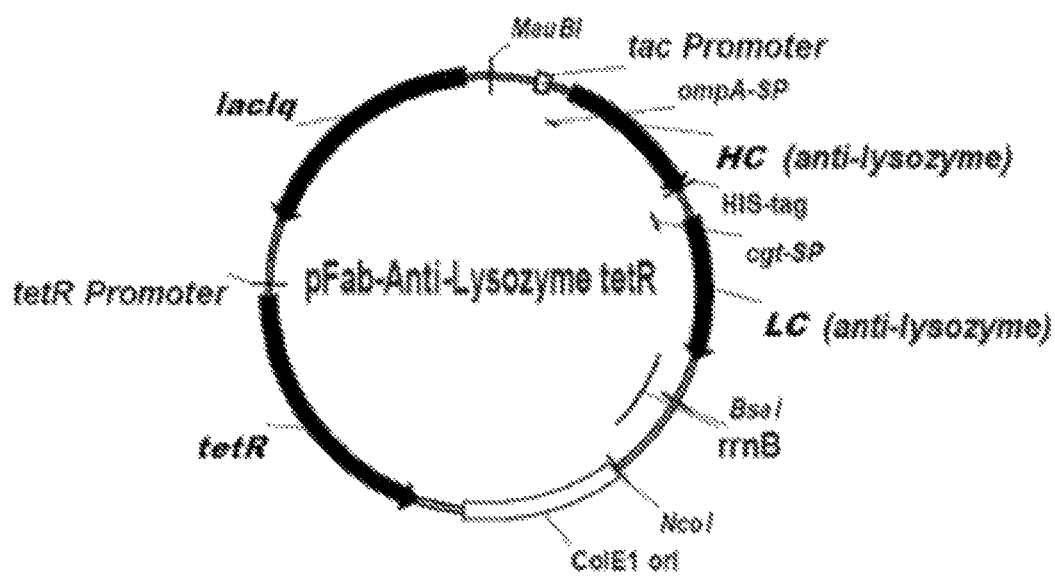

Fig. 8: pcysEX-GAPDH-ORF306_pyrH1_tetR
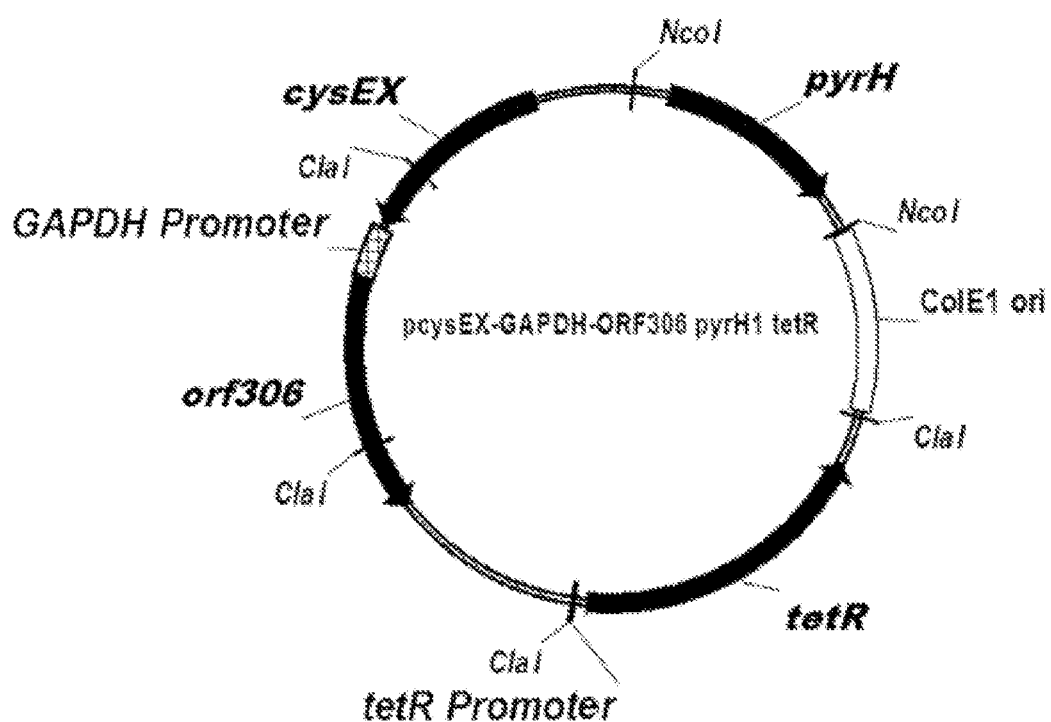

Fig. 9: pCGT_pyrH1_tetR
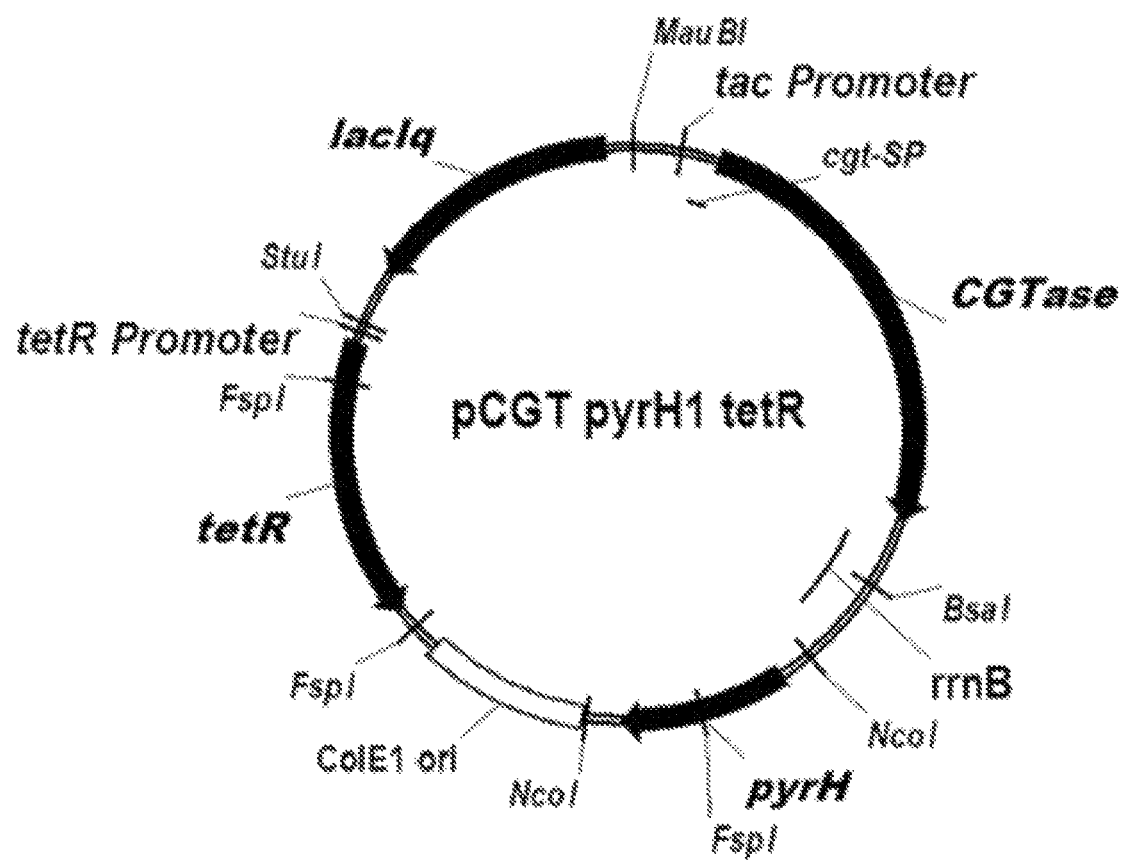

Fig. 10: pFab-anti-Lysozyme_pyrH1_tetR
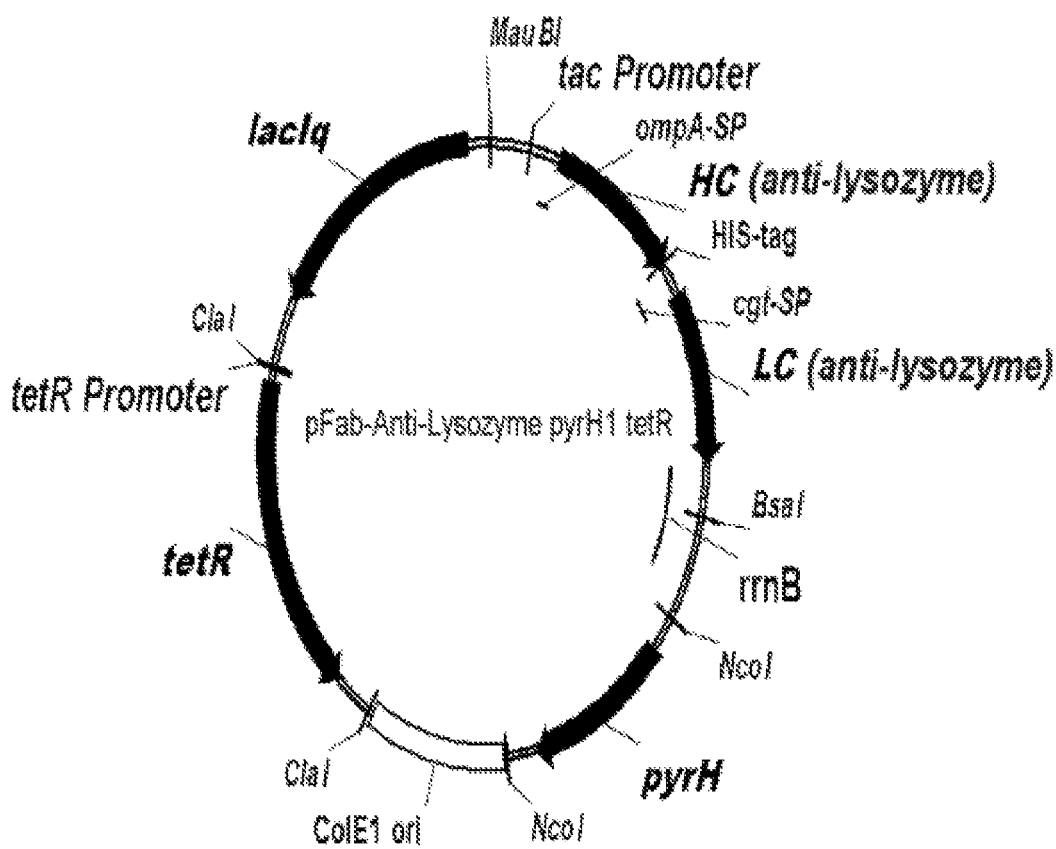

Fig. 11: pcysEX-GAPDH-ORF306_plsC1_tetR
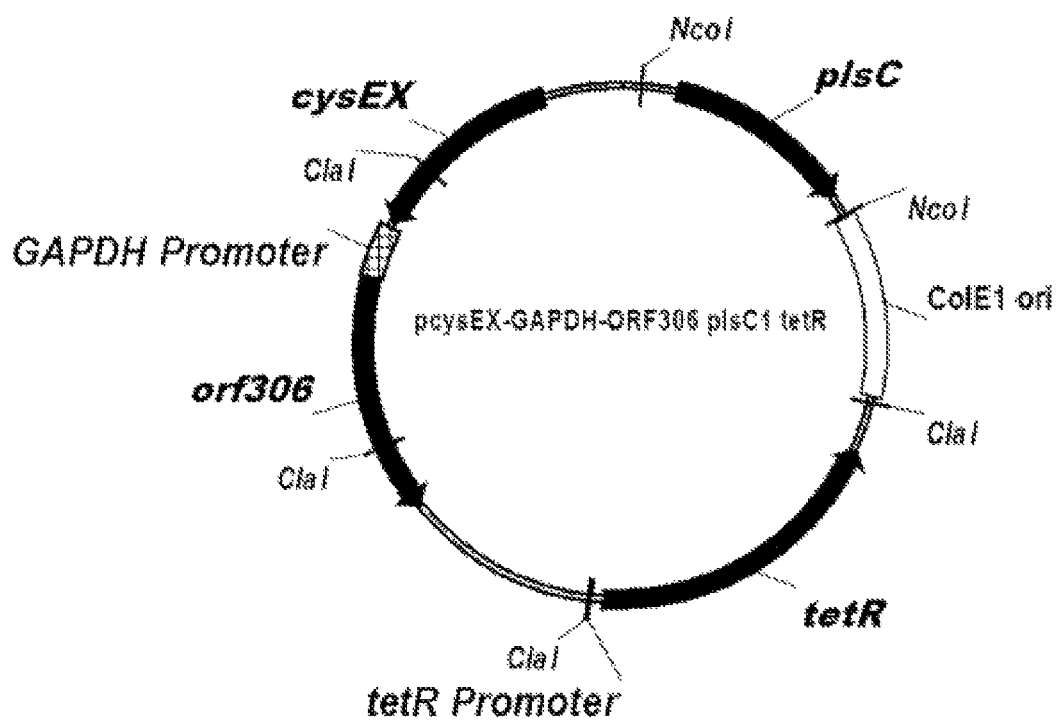

Fig. 12: pCGT_plsC1_tetR
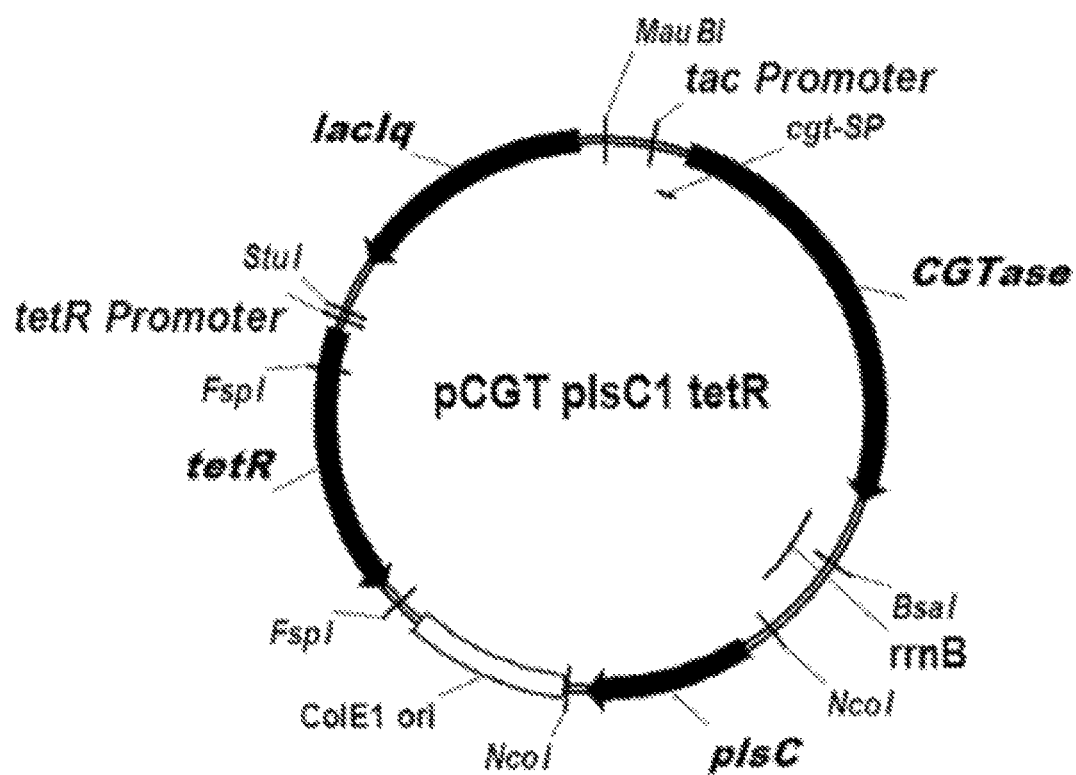

Fig. 13: pFab-anti-Lysozyme_plsC1_tetR
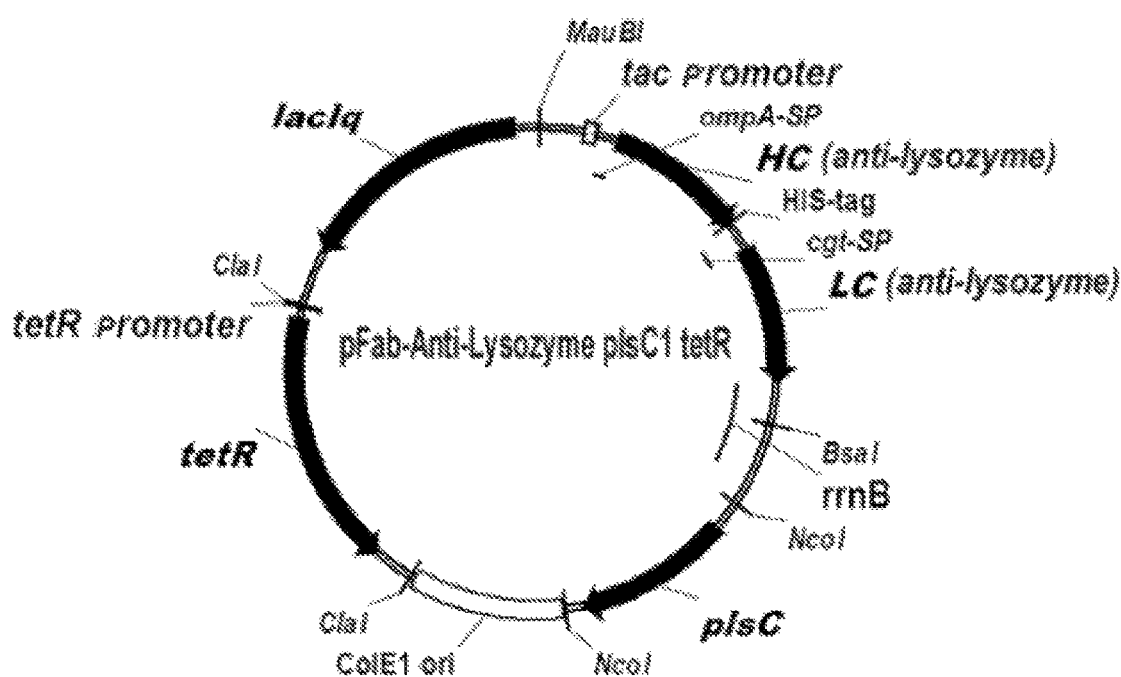

Fig. 14: pcysEX-GAPDH-ORF306_pyrH
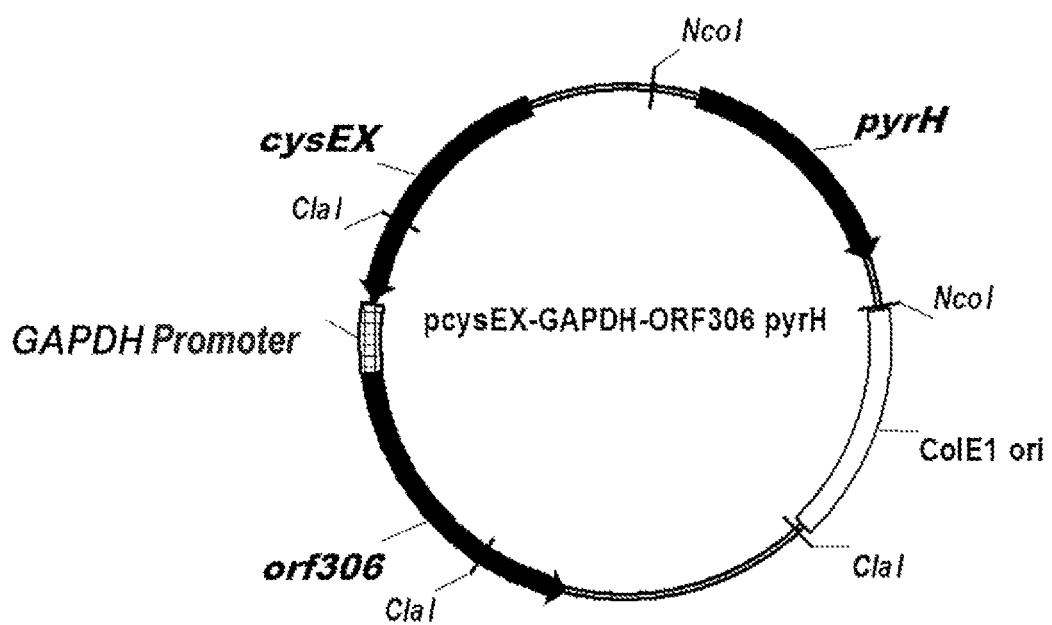

Fig. 15: pCGT_pyrH
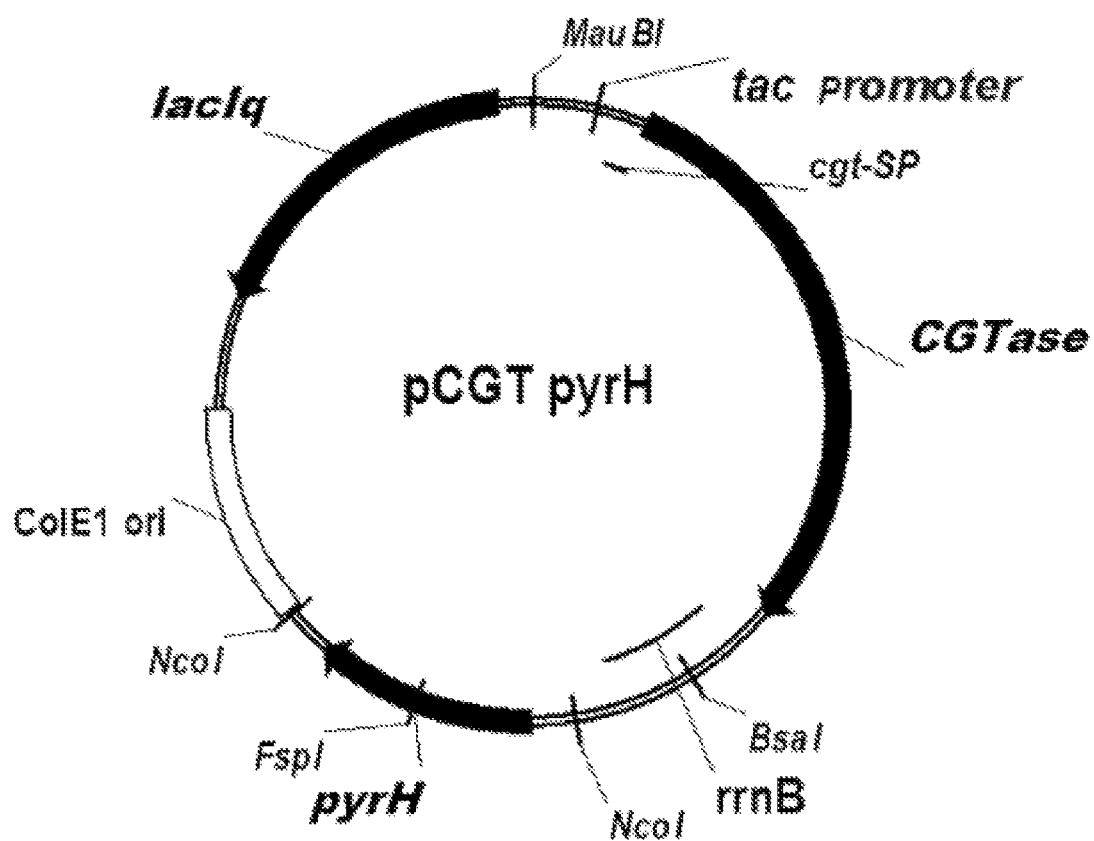

Fig. 16: pFab-anti-Lysozyme_pyrH
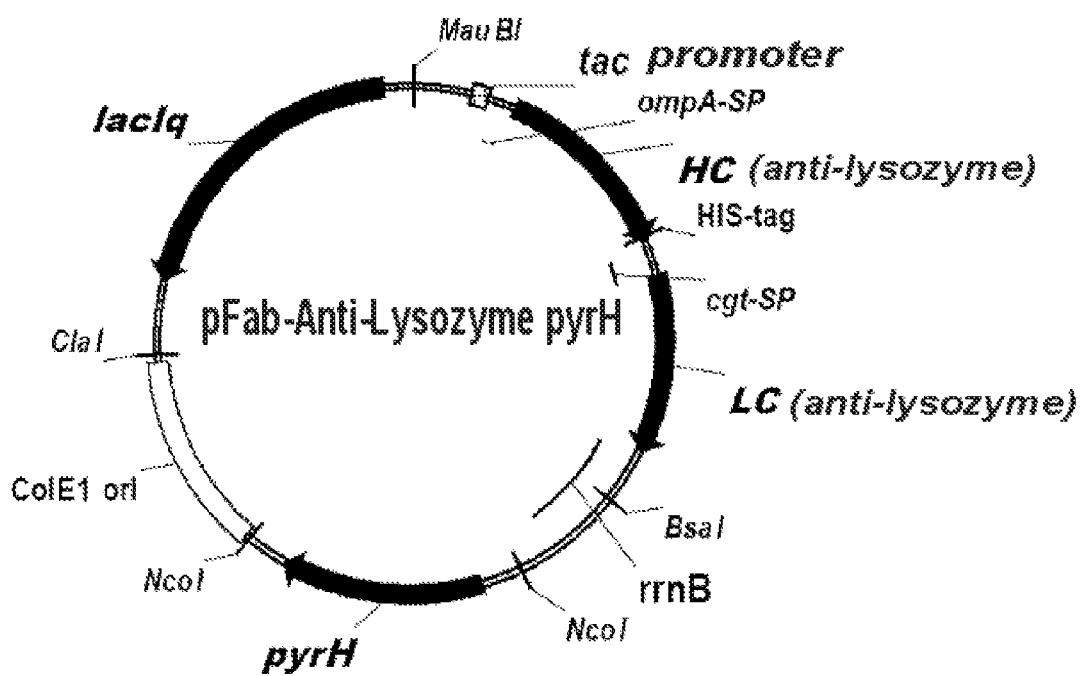

Fig. 17: pcysEX-GAPDH-ORF306_plsC
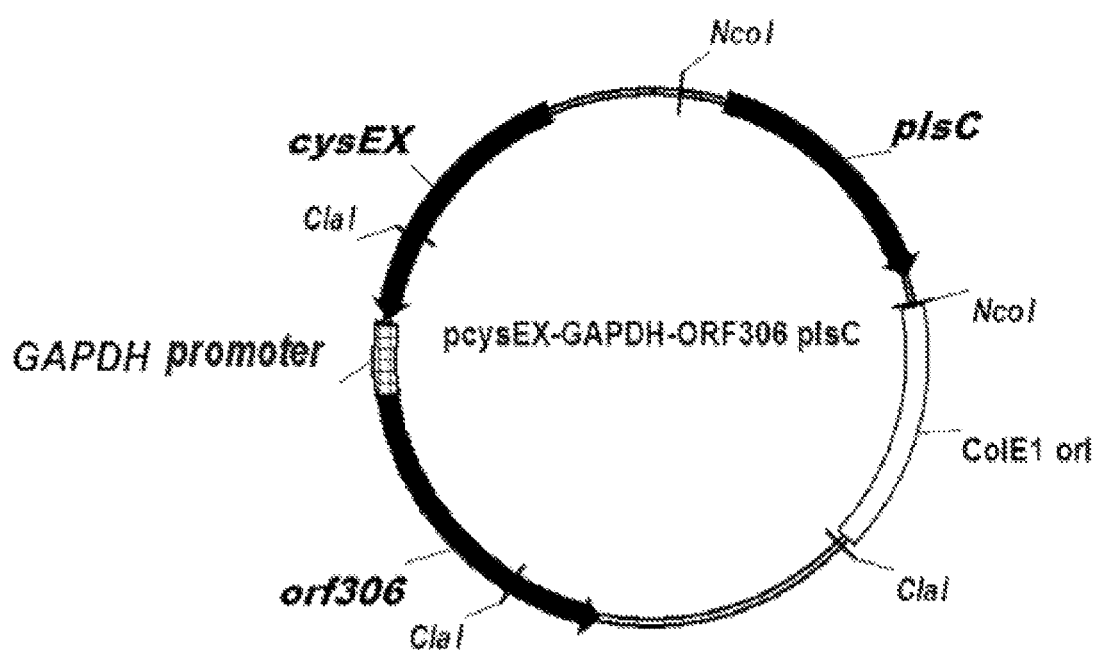

Fig. 18: pCGT_plsC
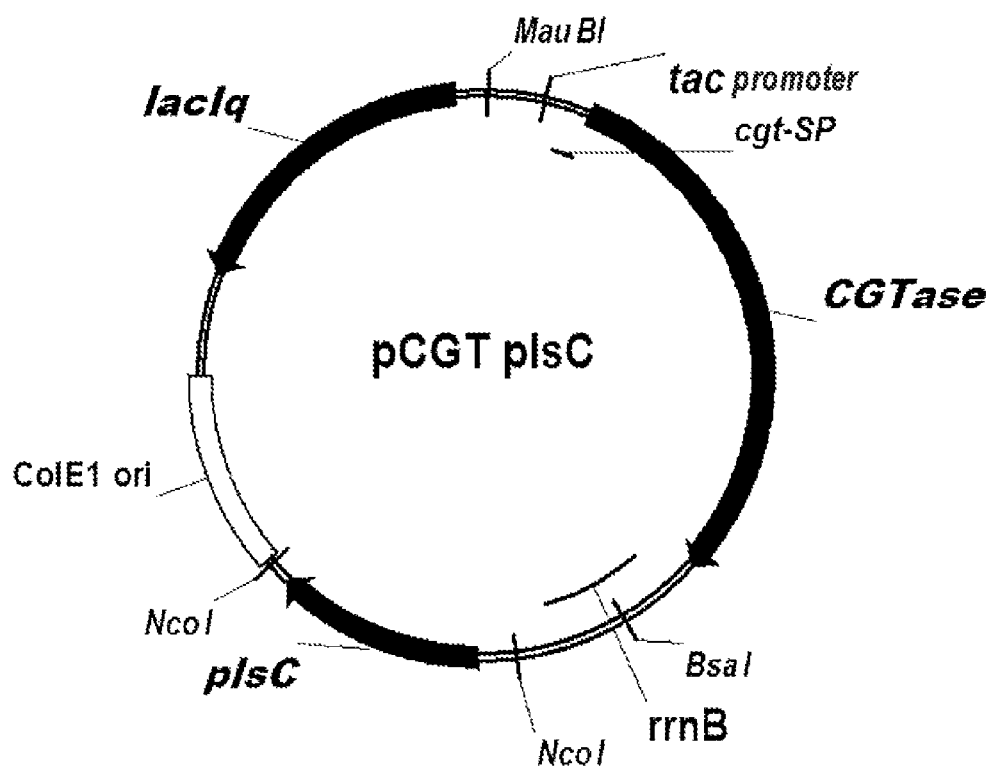

Fig. 19: pFab-anti-Lysozyme_plsC
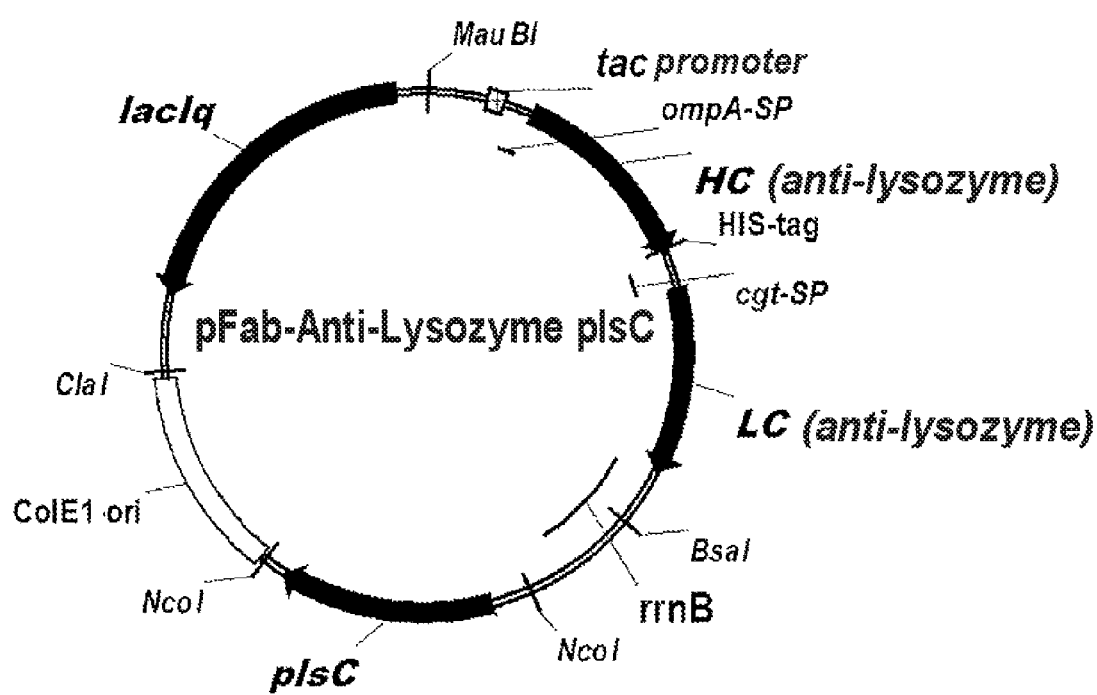

MICROORGANISM STRAIN AND METHOD FOR ANTIBIOTIC-FREE, FERMENTATIVE PREPARATION OF LOW MOLECULAR WEIGHT SUBSTANCES AND PROTEINS

CROSS-REFERENCE TO RELATED APPLICATIONS

This application is a U.S. National Phase Application of PCT/EP2015/079488, filed Dec. 11, 2015, the contents of which are incorporated herein by reference in their entireties for all purposes.

SEQUENCE LISTING STATEMENT

Incorporated herein by reference in its entirety is a Sequence Listing named "W115420137_Sequence-Listing_ST25", which is being submitted to the USPTO via EFS-web on even date herewith as an ASCII text file 15.9 KB in size. This file, which was created on May 7, 2018, constitutes both the paper and computer readable form of the Sequence Listing.

BACKGROUND OF THE INVENTION

The invention relates to a microorganism strain and to a method for the antibiotic-free fermentative production of low-molecular-weight substances and proteins.

Principally, the natural production of low-molecular-weight substances with the aid of microorganisms has increased and the market for recombinant protein pharmaceuticals ("biologics") has also shown strong growth in recent years. Owing to the high cost pressure in fermentative production, especially for active pharmaceutical ingredients based on protein, there is an ongoing search for more efficient and thus more cost-effective methods and systems for the production thereof. Various microorganisms, such as bacteria, yeasts, filamentous fungi or else plant cells or animal cells, can be used as producers. Here, what is crucial from an economic point of view is a cost-effective fermentation, high product yields and, in the case of proteins, a correct folding and/or modification that leads to a functional protein. Owing to its very extensively studied genetics and physiology, the short generation time and the simple handling, the Gram-negative enterobacterium *Escherichia coli* (*E. coli*) is currently the most frequently used organism for the production of low-molecular-weight substances and proteins.

Fundamentally, two different microorganisms are used: the microorganisms which naturally produce the substances and those which have been genetically modified. The technical methods required for genetic modification have been known for a long time in the prior art. The goal here is to introduce the genes required for the target proteins or for the synthesis of the low-molecular-weight substances into the host cell. Said genes are transcribed by the host cell, translated, modified where necessary, and possibly outwardly transferred into the medium.

The economic viability of a biotechnological method depends crucially on the product yields achieved. Said yields can be optimized via the expression system (host cell, genetic elements, etc.), the fermentation parameters and the culture media.

Basically, the host cells can be modified in two different ways. Thus, the new genetic information can be integrated into the genome (filamentous fungi, yeasts, etc.) and/or be introduced on an extrachromosomal element (e.g., plasmid) (prokaryotes, yeasts, etc.). In the case of the genetic integration of the genes into the genome, said genes are maintained well in the host cell even in the absence of selection pressure. However, a disadvantage is that, in the case of prokaryotes, there is only one copy of the gene in the host and the integration of further copies of the same gene to increase product formation via the gene-dosage effect is very challenging owing to sequence-specific recombination events (EP 0284126 B1).

When using extrachromosomal DNA, the genetic information of the target protein in the form of a plasmid is generally transformed into the *E. coli* production strain. Since the gene-dosage effect has an effect here too, a highest possible number of plasmid copies per cell is striven for. Since such a genetic element is easily lost from the cell owing to the stress, both due to the replication of the plasmid and due to the production of the target protein, it is necessary to exert a selection pressure over the entire cultivation. It is standard to use, as selection markers, antibiotic resistance genes, which thus make it possible for the cell comprising such an element to grow in the presence of antibiotics. Accordingly, only the cells bearing a plasmid can multiply. Since the ability to produce the target substance or the target protein is also lost as a result of the loss of plasmid, this has a direct effect on the yields which can be achieved in the fermentation.

In recent years, the use of antibiotic resistances as selection markers has been increasingly viewed critically. Firstly, the use of antibiotics is rather expensive, especially when the resistance is based on an antibiotic-degrading enzyme, since it is necessary to constantly provide additional dosages of the antibiotic. Secondly, the widespread use in medicine and other fields contributes to the spread of the resistance genes to other strains, in some cases pathogenic ones. This has negative consequences for the treatment of diseases.

Meanwhile, antibiotic-free selection systems have also been developed in the prior art. Multiple different antibiotic-free systems have been developed. These can be divided into three different basic systems. The use of auxotrophies, toxin-antitoxin systems and other methods.

The category of other methods covers mechanisms which do not follow a general principle, for example suppressor tRNAs, fab I/triclosan (FA synthesis), operator/repressor titration (Peubez et al. Microbial Cell Fac, 2010, 9:65). However, these methods are generally used for the synthesis of DNA and DNA fragments for gene therapy and are not optimized for the production of high yields of target substances. In some cases, what are used for selection, instead of antibiotics, are other substances, for example triclosan, herbicides and heavy metals, which, however, also raise health concerns. For example, Herrero et al. (1990, J. Bacteriol. 172, 6557-6567) describe resistance genes against herbicides and heavy metals as selection markers.

Toxin-antitoxin systems (Hok-Sok, ccdA/B, etc.) consist of two genetic elements, it being possible for both to be encoded on the plasmid or for them to be encoded chromosomally and on the plasmid (Gerdes et al. Proc Natl Acad Sci USA, 1986, 83:3116-20). Here, the antitoxin has a neutralizing effect on the toxin. In the event of loss of the plasmid, this mechanism is missing and the plasmid-free cell dies because of the chromosomally encoded and long-living toxin.

A further known selection method is the complementation of auxotrophic strains. Here, genes in the genome of the production strain that have essential functions in metabolism are removed or inactivated. Accordingly, such genes are referred to as essential genes. The resulting auxotrophic strains can only grow, multiply or survive when the metabolic function is circumvented or re-established. This can be achieved either by feeding appropriate precursors or end products of the metabolism (amino acids, bases, etc.) or by introducing the gene which was deactivated in the host genome. The patent EP 0284126 B1 names auxotrophy markers of amino acid metabolism. Since auxotrophies can be easily supplemented by addition of the necessary metabolic product into the medium, these strains can be generated easily. This is because the cells can be cultivated in the presence of the metabolic product even in the absence of plasmid. By means of transformation, the information for the synthesis of the amino acid/base is re-introduced into the cell and the cell can grow even in the absence of supplementation. Accordingly, the selection must be done on minimal media without the supplement.

In practice, it has so far not been possible to implement the use of such auxotrophies as selection markers, since media having a complex composition are usually used in industrial fermentation. Here, for cost reasons, waste products are generally a constituent of the fermentation medium, such as, for example, residues of cereal (ethanol production), corn (starch production), potatoes (starch recovery) or yeast extract. These serve both as carbon sources and as nitrogen sources. In some cases, these constituents are not precisely defined, but contain amino acids, bases, vitamins, etc., which can be taken up from the medium. Therefore, it is difficult in industrial fermentation, if not impossible, to build up a sufficient selection pressure with auxotrophic strains.

The use of an auxotrophy in glucose metabolism, as described in WO 2008/135113 A1, has, too, insufficient selectivity in the media that are used industrially. Although the microorganisms can grow particularly well on glucose and multiply more rapidly than is the case in media containing other carbon sources, this advantage is nullified because of the higher stress due to the plasmid or the production of the target substance. Other carbon sources are available in complex media and are used by the cells.

This also applies to the use of the pyrC gene (dihydroorotase) as auxotrophy marker, as described in WO 07039632 A1. This enzyme is present at the start of the synthesis of pyrimindine bases and inactivation also leads to the inhibition of de novo synthesis. However, the bases can be taken up from the medium and utilized and an appropriate selection pressure cannot be built up in industrial media.

Exceptions are auxotrophies for the essential thymidine and D-alanine, which, even in complex constituents, only occur in traces or not at all in the fermentation media (EP 0251579 A1; EP 0185512 B1). But these systems too are not suitable for efficient production in the high-cell-density method, which is generally striven for. Since, in said method, some cells die and lyse, there is accordingly release of thymidine and D-alanine or other amino acids, etc., which can in turn supplement the auxotrophies.

Overall, it has to be stated that, despite years of experience in the fermentative production of low-molecular-weight substances and proteins, no universally usable system has been developed to date, apart from that via substances which are expensive or represent a risk to health and/or the environment, such as antibiotics. Owing to the complex growth media used in industry, the various approaches for selection via auxotrophy markers have, too, only led to poor results to date.

This applies principally to microorganisms, but especially to less robust production strains, such as, for example, leaky strains, which are used because of their special properties (release of proteins into the medium). In the case of the industrial use of said strains on an industrial scale, use is usually made of complex constituents in the medium.

For the production of products used industrially, the use of defined media composed of purified constituents is not economical for cost reasons.

BRIEF SUMMARY OF THE INVENTION

It is an object of the invention to provide a microorganism strain for the production of low-molecular-weight substances or proteins, which strain remains stable even in media containing complex constituents and in which strain the production plasmid is not stabilized in the cell by an antibiotic/resistance marker system.

This object is achieved by a microorganism strain containing in its genome a mutation in a gene, which mutation brings about an auxotrophy in the strain, and also a production plasmid encoding at least one enzyme for the production of a low-molecular-weight substance or at least one recombinant protein and also a functional copy of the gene, the chromosomal inactivation of which brings about the auxotrophy, characterized in that the auxotrophy is a nonfeedable auxotrophy.

In the context of the invention, a nonfeedable auxotrophy is to be understood to mean that the auxotrophy reduces the growth of the microorganism cell or brings about the death of the microorganism cell and is not supplementable by addition of metabolism-specific precursors, intermediates and/or end products to the growth medium.

In the context of the invention, there is a reduced growth when the growth rate of the strain in a fermentation is lowered to ≤10% after the mutation of the gene in comparison with the growth rate of the strain before the mutation of the gene, preferably when there is no more growth.

Particularly preferably, the mutation leads to the inactivation of a gene, brings about in this way a nonfeedable auxotrophy and thus the death of the microorganism cell. In the genome of a cell of the microorganism strain according to the invention, there is therefore inactivation of a gene which is essential for an anabolic metabolic pathway necessary for the growth or survival of the cell, it not being possible for growth or survival of the cell to be achieved again by addition of metabolism-specific precursors, intermediates and/or end products to the growth medium.

A nonfeedable auxotrophy gene in the context of the invention is a gene in the genome of a microorganism cell, the inactivation of which cannot be complemented by addition of metabolism-specific precursors, intermediates and/or end products to the growth medium and the inactivation of which leads to a reduced growth rate or to the death of the microorganism cell.

Preferably, the mutation of the gene, which mutation brings about the nonfeedable auxotrophy in the strain, leads to the inactivation of said gene or to the inactivation of the activity of the gene product coded by the gene.

Examples of nonfeedable auxotrophy genes (lethal genes) are described in Baba et al. (2006, Mol. Syst. Biol. 2:2006.0008). Preferably, the genes are the genes map, pyrH, ftsL, rpsB, tsf, plsC or homologous genes thereof.

Particularly preferably, the gene is the pyrH gene or the plsC gene or homologous genes with identical function or activity.

A gene in the context of the present invention comprises not only the DNA segment which is transcribed, but also the DNA segments which are involved in the regulation of this copying process, i.e., the regulatory elements of the gene, such as, preferably, promoters and terminators.

Homologous genes are preferably to be understood to mean genes which code for a protein having the same activity as the protein coded by the stated gene and have a sequence identity greater than 30%, particularly preferably greater than 70%, in relation to the sequences of the stated genes in the microorganism in question, which sequences are in each case known from databases.

The pyrH gene codes for the enzyme UMP kinase (EC: 2.7.4.22; UK, uridine monophosphate kinase, uridylate kinase, uridine 5'-monophosphate (UMP) kinase). Said enzyme activates UMP to form UDP using ATP. In a next step, UDP is activated by a further kinase (UDP kinase) to form UTP, which can be used both for the synthesis of RNA and for the synthesis of CTP (cytosine triphosphate) and TTP (thymidine triphosphate). CTP and TTP are in turn a constituent of RNA (CTP) and DNA (dCTP and dTTP). UMP is thus the origin of pyrimidine building blocks of RNA and DNA. Since a conversion of uracil into cytosine or thymidine only takes place at the triphosphate level, a deactivation of UMP kinase leads to a complete block of this synthetic pathway. Fundamentally, the cell can take up only the monophosphates of the three bases from the medium. For the conversion of UMP to UTP, UMP kinase is essential. This means that this auxotrophy is not supplementable by feeding and is thus independent of the media composition.

The pyrH gene is characterized by SEQ ID No. 1. The pyrH gene product (PyrH) is characterized by SEQ ID No. 2.

In the context of the present invention, pyrH homologs are genes which code for a protein having PyrH activity and which have a sequence identity greater than 30% in relation to SEQ ID No. 1. Particular preference is given to a sequence identity greater than 70% in relation to SEQ ID No. 1. The pyrH gene is especially preferred.

PyrH homologs are proteins having a sequence identity greater than 30% in relation to SEQ ID No. 2, which proteins have a UMP kinase activity as per EC number 2.7.4.22. Particularly preferably, PyrH homologs have a UMP kinase activity as per EC number 2.7.4.22 and a sequence identity greater than 70% in relation to SEQ ID No. 2. The PyrH protein is especially preferred.

The PyrH activity in a cell can be determined according to the assay described by Bucurenci et al. (1998, J. Bact. 180: 473-77).

The plsC gene codes for the enzyme 1-acylglycerol-3-phosphate O-acyltransferase (EC: 2.3.1.51). Said enzyme transfers one fatty acid from acyl-CoA to one acylglycerol-3-phosphate with release of one CoA-SH. The resulting diacylglycerol-3-phosphate is used for the synthesis of essential membrane constituents such as triglycerides and glycerophospholipids. This means that this step is necessary for the production of the membrane systems of *E. coli*. In *E. coli*, although an uptake of fatty acids is possible, triglycerides and glycerophospholipids must be synthesized in the cell or in the membrane.

The plsC gene is characterized by SEQ ID No. 3. The plsC gene product (PlsC) is characterized by SEQ ID No. 4.

In the context of the present invention, plsC homologs are genes which code for a protein having PlsC activity and which have a sequence identity greater than 30% in relation to SEQ ID No. 3. Particular preference is given to a sequence identity greater than 70% in relation to SEQ ID No. 3. The plsC gene is especially preferred.

PlsC homologs are proteins having a sequence identity greater than 30% in relation to SEQ ID No. 4, which proteins have a 1-acylglycerol-3-phosphate O-acyltransferase activity as per EC number 2.3.1.51. Particularly preferably, PlsC homologs have a 1-acylglycerol-3-phosphate O-acyltransferase activity as per EC number 2.3.1.51 and a sequence identity greater than 70% in relation to SEQ ID No. 4. The PlsC protein is especially preferred.

The PlsC activity in a cell can be determined according to the assay described by Monrand et al. (1998, Biochem. Biophys. Res. Commun. 244: 79-84).

The degree of DNA identity is determined by means of the program "nucleotide blast", which can be found on the webpage blast.ncbi.nlm.nih.gov/ and which is based on the blastn algorithm. The default parameters were used as algorithm parameters for an alignment of two or more nucleotide sequences. The default general parameters are: Max target sequences=100; Short queries="Automatically adjust parameters for short input sequences"; Expect Threshold=10; Word size=28; Automatically adjust parameters for short input sequences=0. The corresponding default scoring parameters are: Match/Mismatch Scores=1, −2; Gap Costs=Linear.

For the comparison of protein sequences, the program "protein blast", on the webpage blast.ncbi.nlm.nih.gov/, is used. Said program relies on the blastp algorithm. The default parameters were used as algorithm parameters for an alignment of two or more protein sequences. The default general parameters are: Max target sequences=100; Short queries="Automatically adjust parameters for short input sequences"; Expect Threshold=10; Word size=3; Automatically adjust parameters for short input sequences=0. The default scoring parameters are: Matrix=BLOSUM62; Gap Costs=Existence: 11 Extension: 1; Compositional adjustments=Conditional compositional score matrix adjustment.

To produce a strain according to the invention, a temperature-sensitive plasmid which has a functional copy of a nonfeedable auxotrophy gene which is to be mutated or deleted is introduced into a suitable microorganism strain. Subsequently, the corresponding nonfeedable auxotrophy gene in the genome of the strain is inactivated. Thereafter, the temperature-sensitive plasmid is exchanged in said strain at a nonpermissive temperature for a production plasmid, wherein the production plasmid encoding at least one enzyme for the production of a low-molecular-weight substance or at least one recombinant protein also contains a functional copy of the nonfeedable auxotrophy gene.

This method ensures that the production plasmid during a fermentation process for the production of low-molecular-weight compounds or of recombinant proteins is maintained stably in the cell even in complex media. Thus, strains according to the invention can be cultivated in the absence of an added selective agent or of an auxotrophy-compensating additive without loss of plasmid.

Fundamentally, any microorganism strain having a gene, the inactivation of which leads to a nonfeedable auxotrophy of the strain, is suitable as starting strain for the production of a strain according to the invention.

Preferably, the starting strain for the generation of a strain according to the invention is an Enterobacteriaceae strain, especially preferably a strain of the species *Escherichia coli*.

The *E. coli* strains that are preferred are those which have a "leaky" mutation. A "leaky mutation" is to be understood to mean a mutation in a gene for a stuctural element of the outer cell membrane or of the cell wall, selected from the group of the omp genes, tol genes, excD gene, excC gene, lpp gene, pal gene, env genes and lky genes, which mutation leads to the cells releasing periplasmic proteins into the medium to an increased extent (Shokri et al., Appl. Microbiol. Biotechnol. 60 (2003), 654-664). Preferably, the "leaky" mutation is a mutation in the lpp gene, particularly preferably a mutation selected from the group consisting of lpp1 mutation, lpp deletion mutation and mutation of the glycine residue at position 14 of the Lpp protein (numbering system including the signal peptide), such as, for example, the lpp-3 mutation. An lpp1 mutation is a mutation in the lpp gene that leads to a substitution of the arginine residue at position 77 with a cysteine residue, an lpp3 mutation is a mutation in the lpp gene that leads to a substitution of the glycine residue at position 14 with an apartic acid residue. These mutations are described in detail in US2008254511. The lpp deletion mutation is preferably a deletion of at least one nucleotide in the lpp gene itself or in the promoter region of the lpp gene that leads to the cells exhibiting an increased leakiness for periplasmic proteins.

In the context of the present invention, increased leakiness is to be understood to mean that, after a fermentation of the cells, there is a higher concentration of periplasmic proteins, for example of alkaline phosphatase, in the culture medium than in the case of a fermentation of the E. coli strain W3110 (ATCC 27325) under the same conditions.

Methods for inactivating a gene in a microorganism strain are known in the prior art. They are described in detail below for the mutation of the two preferred genes (pyrH gene and plsC gene) and also the gene products thereof. It is also possible to apply these methods in an analogous manner to other genes, the inactivation of which brings about a nonfeedable auxotrophy of a microorganism strain.

The temperature-sensitive plasmid contains a temperature-sensitive origin of replication and a functional copy of the nonfeedable auxotrophy gene. In addition, said plasmid contains a selection marker gene for the selection of transformants. The selection marker is, for example, an antibiotic resistance.

A preferred example of a temperature-sensitive origin of replication is "oriR101 & repA101-ts", a derivative of the origin of replication of plasmid pSC101 (Hashimoto-Gotoh et al.; Gene, 2000, 241:1:185-191), which is located, inter alia, on the plasmids pKD20 and pKD46 (Datsenko and Wanner, 2000, P.N.A.S. 97: 6640-6645).

The temperature-sensitive plasmid is introduced into the cell using a transformation technique known to a person skilled in the art, for example TSS method, CaCl/RbCl method, electroporation method.

Selection is carried out for cells containing the temperature-sensitive plasmid by means of the selection marker present on the temperature-sensitive plasmid, whereas the cells are incubated at a temperature permissive for the plasmid.

Such a temperature-sensitive plasmid can be exchanged for the production plasmid by cultivating the microorganism strain after the transformation with the production plasmid at a temperature which is nonpermissive for the temperature-sensitive plasmid. A preferred nonpermissive temperature range is 37-45° C., particularly preferably 39-43° C.

The production plasmid is introduced into the cell using a transformation technique known to a person skilled in the art, for example TSS method, CaCl/RbCl method, electroporation method.

The transformants can be cultivated both on agar plates and in liquid culture. In a preferred embodiment, the microorganism strain is exposed, immediately after the transformation with the production plasmid, to a temperature shock at 47-55° C., preferably at 52° C., for 30-90 min, preferably 60 min. The further incubation is then carried out at the abovementioned nonpermissive temperature. As a result, the temperature-sensitive plasmid is exchanged for the production plasmid in one step and a production strain according to the invention for the antibiotic-free production of low-molecular-weight substances or recombinant proteins is generated.

For example, one of the following known expression vectors is used as production plasmid: pJF118EH, pKK223-3, pUC18, pBR322, pACYC184, pASK-IBA3 or pET.

The production plasmid contains, besides the functional copy of the nonfeedable auxotrophy gene, one or more target genes and also the expression signals necessary for the expression of said target genes, such as, for example, promoter sequences, operator sequences and terminator sequences. The target genes code for at least one enzyme for the production of a low-molecular-weight substance or at least one recombinant protein.

The low-molecular-weight substances are basic building blocks (bases, amino acids, fatty acids, etc.) and also secondary metabolites (vitamins, antioxidants, etc.) which the organism can synthesize. Preference is given to amino acids, particular preference is given to the amino acid L-cysteine and compounds derived therefrom.

The recombinant proteins are preferably heterologous proteins.

A heterologous protein is to be understood to mean a protein which does not belong to the proteome, i.e., to the entire natural protein makeup, of the host organism.

Preferably, the heterologous protein is a eukaryotic protein, particularly preferably a protein which contains one or more disulfide bonds or which is present in its functional form as a dimer or multimer, i.e., the protein has a quaternary structure and is constructed from multiple identical (homologous) or nonidentical (heterologous) subunits.

A preferred class of proteins consisting of multiple protein subunits are antibodies or fragments of antibodies. Particular preference is given to functional Fab antibody fragments.

There follows a description of the production of a microorganism strain according to the invention, in which the nonfeedable auxotrophy gene pyrH has been mutated.

Fundamentally, any host organism having a gene for the UMP kinase PyrH is suitable as starting strains for the production of a microorganism strain according to the invention that has a genomic pyrH inactivation.

Methods for inactivating the pyrH gene in a microorganism strain are known in the prior art. For example, the pyrH gene can be inactivated by introducing a mutation (substitution, insertion or deletion of individual or multiple nucleotides) into the reading frame of the pyrH gene, which mutation leads to the specific activity of PyrH being inactivated. A person skilled in the art is aware of methods for generating such pyrH alleles. For example, it is possible, by means of the method described in Link et al. (1997, J. Bacteriol. 179: 6228-37), to insert chromosomal mutations into a gene via the mechanism of homologous recombination. The chromosomal deletion of the entire pyrH gene or of a portion thereof is, for example, possible with the aid of the λ red recombinase system according to the method described by Datsenko and Wanner (2000, Proc. Natl. Acad. Sci. USA. 97: 6640-5). pyrH alleles can also be transferred via a transduction by means of P1 phages or conjugation from a strain with pyrH mutation to a pyrH wild-type strain, with the pyrH wild-type gene in the chromosome being replaced with the corresponding pyrH allele.

Furthermore, the pyrH gene of a cell can also be inactivated by mutating at least one element necessary for the regulation of expression (e.g., promoter, enhancer, ribosome binding site) by substitution, insertion or deletion of individual or multiple nucleotides. There is an inactivation in the context of the invention when the growth rate of the cells in a fermentation is lowered to ≤10% by the inactivation of the gene in comparison with the cells before the mutation, preferably when there is no more growth.

Particularly preferably, the mutation leads to the death of the microorganism cell.

Since the inactivation of the pyrH gene leads to a non-feedable auxotrophy, a functional copy of the pyrH gene must already be present in the cell before the chromosomal inactivation. This can be achieved by the transient introduction of a temperature-sensitive plasmid containing a functional copy of the pyrH gene.

In such cells containing the temperature-sensitive plasmid, it is then possible, by means of the stated methods, to inactivate the pyrH gene in the genome.

In a further step, said temperature-sensitive plasmid is exchanged for the production plasmid, which also contains a functional copy of the pyrH gene. This is preferably done in the manner already described.

Microorganism strains according to the invention having an inactivated plsC gene or some other mutated nonfeedable auxotrophy gene can be produced in an analogous manner.

In the production of recombinant proteins, a distinction is made between a cytoplasmic production and a secretory production. Whereas the target protein is accumulated in the cytoplasm of the cell in the case of cytoplasmic production, the target protein is translocated into the periplasm or into the culture medium in the case of secretory production. In the context of the invention, secretory production is preferred. The secretory production of the target protein into the culture medium is especially preferred.

For the secretory production of proteins, i.e., for the translocation of the protein from the cytoplasm into the periplasm or the culture medium, it is necessary to link the 5'-end of the gene of the protein to be produced in frame to the 3'-end of a signal sequence for protein export. Suitable for this purpose are principally the genes of all signal sequences which lead, in *E. coli*, to a translocation of the target protein into the periplasm. In *E. coli*, three main translocation pathways are known: the SEC pathway, TAT pathway and SRP pathway. Preference is given to those signal sequences which allow a translocation via the SEC apparatus. Various signal sequences of this kind are described in the prior art, for example the signal sequences of the following genes: phoA, ompA, pelB, ompF, ompT, lamB, malE, dsbA, Staphylococcal protein A, StII and others (Choi and Lee, Appl. Microbiol. Biotechnol. 64 (2004), 625-635).

What is preferred according to the invention is the signal sequence of the phoA gene or of the ompA gene of *E. coli* or the signal sequence for a cyclodextrin glycosyltransferase (CGTase) from *Klebsiella pneumoniae* M5a1, or the sequence derived from this signal sequence, which is disclosed in US2008076157.

The cultivation (fermentation) of the cells containing a production plasmid is done according to customary fermentation methods known to a person skilled in the art in a bioreactor (fermenter) without addition of antibiotics.

The invention also provides a method for producing low-molecular-weight substances or recombinant proteins by means of a microorganism strain, which method is characterized in that a microorganism strain according to the invention is used and an antibiotic-free fermentation medium is used.

The fermentation takes place in a customary bioreactor, for example a stirred tank, a bubble-column fermenter or an airlift fermenter. Preference is given to a stirred tank fermenter on an industrial scale and thus of >100 l in size.

In the fermentation, the cells of the strain according to the invention are cultivated in a liquid medium, with continuous monitoring and precise control of various parameters such as, for example, the supply of nutrients, the partial pressure of oxygen, the pH and the temperature of the culture. The period of the cultivation is preferably 16-150 h, particularly preferably 24-72 h.

Possible fermentation media are all common media known to a person skilled in the art for the cultivation of microorganisms. Said fermentation media are, however, free of any antibiotic.

It is possible to use complex media or minimal salt media, to which a defined proportion of complex components such as, for example, peptone, tryptone, yeast extract, molasses or corn steep liquor is added. Preference is given to a medium containing complex media components.

As primary carbon source for the fermentation, it is possible to use all cell-utilizable sugars, sugar alcohols or organic acids or salts thereof. Preference is given to using glucose, lactose or glycerol. Particular preference is given to glucose and lactose. Also possible is a combined feeding of multiple different carbon sources. The carbon source can be initially charged in full in the fermentation medium at the start of the fermentation, or nothing is initially charged or only a portion of the carbon source is initially charged at the start and the carbon source is fed in over the course of the fermentation. Particular preference is given to an embodiment in which a portion of the carbon source is initially charged and a portion is fed. Particularly preferably, the carbon source is initially charged in a concentration of 10-30 g/l, the feeding is started when the concentration has fallen to less than 5 g/l and is arranged such that the concentration is maintained below 5 g/l.

The partial pressure of oxygen ($pO_2$) in the culture is preferably between 10 and 70% saturation. Preference is given to a $pO_2$ between 20 and 60%; the $pO_2$ is particularly preferably between 45 and 55% saturation.

The pH of the culture is preferably between pH 6 and pH 8. Preference is given to a pH between 6.5 and 7.5; the pH of the culture is particularly preferably between 6.8 and 7.2.

The temperature of the culture is between 15 and 45° C. Preference is given to a temperature range between 18 and 40° C., particular preference is given to a temperature range between 25 and 35° C., very particular preference is given to 30° C.

In a preferred arrangement, the fermentation is a high-cell-density fermentation. A high-cell-density fermentation is to be understood to mean a fermentation, in the course of which cell dry weights of more than 50 g/l are achieved. Particular preference is given to cell dry weights of more than 70 g/l.

BRIEF DESCRIPTION OF THE DRAWINGS

FIG. 1 shows a restriction and function map of plasmid pKD46 from Example 2.

FIG. 2 shows a restriction and function map of the plasmid pAF-ts-pyrH produced in Example 2.

FIG. 3 shows a restriction and function map of the plasmid pAF-ts-plsC produced in Example 2.

FIG. 4 shows a restriction and function map of the plasmid pMT1 used in Example 5.

FIG. 5 shows a restriction and function map of the expression plasmid pcysEX-GAPDH-ORF306_tetR produced in Example 5.

FIG. 6 shows a restriction and function map of the expression plasmid pCGT_tetR produced in Example 6.

FIG. 7 shows a restriction and function map of the expression plasmid pFab-anti-Lysozyme_tetR produced in Example 7.

FIG. 8 shows a restriction and function map of the expression plasmid pcysEX-GAPDH-ORF306 pyrH1_tetR produced in Example 8.

FIG. 9 shows a restriction and function map of the expression plasmid pCGT_pyrH1 tetR produced in Example 8.

FIG. 10 shows a restriction and function map of the expression plasmid pFab-anti-Lysozyme_pyrH1 tetR produced in Example 8.

FIG. 11 shows a restriction and function map of the expression plasmid pcysEX-GAPDH-ORF306_plsC1_tetR produced in Example 8.

FIG. 12 shows a restriction and function map of the expression plasmid pCGT_plsC1 tetR produced in Example 8.

FIG. 13 shows a restriction and function map of the expression plasmid pFab-anti-Lysozyme_plsC1 tetR produced in Example 8.

FIG. 14 shows a restriction and function map of the production plasmid pcysEX-GAPDH-ORF306_pyrH according to the invention produced in Example 9.

FIG. 15 shows a restriction and function map of the production plasmid pCGT_pyrH according to the invention produced in Example 9.

FIG. 16 shows a restriction and function map of the production plasmid pFab-anti-Lysozyme_pyrH according to the invention produced in Example 9.

FIG. 17 shows a restriction and function map of the production plasmid pcysEX-GAPDH-ORF306_plsC according to the invention produced in Example 9.

FIG. 18 shows a restriction and function map of the production plasmid pCGT_plsC according to the invention produced in Example 9.

FIG. 19 shows a restriction and function map of the production plasmid pFab-anti-Lysozyme_plsC according to the invention produced in Example 9.

DETAILED DESCRIPTION OF PREFERRED EMBODIMENTS

The following examples serve to further elucidate the invention. All the molecular biology and microbiology methods used, such as polymerase chain reaction (PCR), gene synthesis, isolation and purification of DNA, modification of DNA by restriction enzymes, Klenow fragment and ligase, transformation, P1 transduction, etc., were carried out in the way which is known to a person skilled in the art, described in the literature or recommended by the respective manufacturers.

Example 1: Amplification of the Marker Gene (pyrH or plsC) with its Own Promoter A DNA fragment of about 1.0 kb in size, coding for the pyrH gene including native promoter region, was amplified using the primers pyrH-NcoI-fw (SEQ ID No. 5) and pyrH-NcoI-rev (SEQ ID No. 6). The template used for the PCR reaction was chromosomal DNA from the *E. coli* strain W3110 (ATCC 27325).

The PCR fragment of about 1.0 kb in size was purified via an agarose gel electrophoresis and isolated from the agarose gel using the "QIAquick Gel Extraction Kit" (Qiagen GmbH, Hilden, Germany) according to the information from the manufacturer. Thereafter, the purified PCR fragment was digested using the restriction enzyme NcoI and stored at −20° C. In an analogous manner, a DNA fragment of about 1.0 kb in size, coding for the plsC gene including native promoter region, was amplified, purified, digested and stored. For the amplification, the primers plsC-NcoI-fw (SEQ ID No. 7) and plsC-NcoI-rev (SEQ ID No. 8) were used.

Example 2: Generation of the Plasmids pAF-Ts-pyrH and pAF-Ts-plsC with Temperature-Sensitive Origin of Replication The starting plasmid used for the construction of the plasmids pAF-ts-pyrH and pAF-ts-plsC with temperature-sensitive origin of replication was the plasmid pKD46 (Datsenko and Wanner, 2000, P.N.A.S. 97: 6640-6645). A restriction and function map of plasmid pKD46 is shown in FIG. 1. The PCR products described in Example 1 and digested using NcoI, which PCR products code for the pyrH gene or plsC gene with its own promoter, were cloned into the NcoI restriction site of pKD46. The ligation preparations were transformed into "DH5α™-T1R *E. coli* cells" (Life Technologies GmbH), multiplied in said cells, and the DNA sequence of the isolated plasmids was verified by means of sequencing. Two of the altogether 4 possible constructs which were generated in this manner have the designations pAF-ts-pyrH and pAF-ts-plsC (see FIGS. 2 and 3).

Example 3: Transformation of Selected *E. coli* Strains Using pAF-Ts-pyrH or pAF-Ts-plsC The plasmids pAF-ts-pyrH and pAF-ts-plsC with temperature-sensitive origin of replication that are described in Example 2 were transformed into the two *E. coli* strains W3110 (ATCC 27325) and W3110lpp3 (described in US2008076158 A1 as "leaky" strain) using the $CaCl_2$ method known to a person skilled in the art. The transformed cells were selected on LB agar plates containing 100 mg/l ampicillin. The strains generated in this manner have the designations W3110/pAF-ts-pyrH, W3110lpp3/pAF-ts-pyrH, W3110/pAF-ts-plsC and W3110lpp3/pAF-is-plsC.

Example 4: Deletion of the Gene pyrH (Inactivation of Uridylate Kinase) or of the Gene plSC (Inactivation of 1-Acylglycerol-3-Phosphate O-Acyltransferase) in *E. coli*

A) Deletion of the Gene pyrH

The gene pyrH, which codes for the enzyme uridylate kinase (PyrH) in *E. coli*, was deleted in the *E. coli* strains W3110/pAF-ts-pyrH and W3110lpp3/pAF-ts-pyrH according to the "λ red method" developed by Datsenko and Wanner (Datsenko and Wanner, 2000, P.N.A.S. 97: 6640-6645). A DNA fragment coding for the kanamycin resistance marker gene (kanR) was amplified using the primers pyrH-fw (SEQ ID No. 9) and pyrH-rev (SEQ ID No. 10). The primer pyrH-fw codes for a sequence consisting of 30 nucleotides that is homologous to the 5'-end of the pyrH gene and a sequence comprising 20 nucleotides that is complementary to a DNA sequence encoding one of the two FRT sites (FLP recognition target) on the plasmid pKD13 (*Coli* Genetic Stock Center (CGSC) No. 7633). The primer pyrH-rev codes for a sequence consisting of 30 nucleotides that is homologous to the 3'-end of the pyrH gene and a sequence comprising 20 nucleotides that is complementary to a DNA sequence encoding the second FRT site on the plasmid pKD13.

The amplified PCR product was introduced by means of electroporation into the *E. coli* strains W3110/pAFts-pyrH and W3110lpp3/pAF-ts-pyrH (see Example 3). The selection for cells with chromosomal integration of the kanamycin resistance marker gene (kanR) was done on LB agar plates containing 50 mg/l kanamycin and 100 mg/l ampicillin. The removal of the chromosomally introduced kanamycin resistance marker gene (kanR) was achieved using the enzyme FLP recombinase, which is encoded on the plasmid pCP20 (CGSC No. 7629). The selection for pCP20-containing cells was done on LB agar plates containing 100 mg/l ampicillin (selection for pAF-ts-pyrH) and 34 mg/l chloramphenicol (selection for pCP20). Owing to a temperature-sensitive origin of replication (ori), the plasmid pCP20 can, after transformation has been carried out, be removed by cultivating the *E. coli* cells at a nonpermissive, i.e., elevated temperature, for example at 42° C.

A first selection for loss of the temperature-sensitive plasmid pCP20 with simultaneous maintenance of the temperature-sensitive plasmid pAF-ts-pyrH was done on LB agar plates containing 100 mg/l ampicillin (selection for pAF-ts-pyrH). Later on, the preselected ampicillin-resistant bacteria clones were checked for kanamycin sensitivity, i.e., the loss of the chromosomally introduced kanamycin marker gene, and for chloramphenicol sensitivity, i.e., the loss of the temperature-sensitive plasmid pCP20.

Only kanamycin- and chloramphenicol-sensitive but ampicillin-resistant clones were finally checked for the chromosomal deletion of the pyrH gene using the primers pyrH-check-for (SEQ ID No. 11) and pyrH-check-rev (SEQ ID No. 12). The template used for the checking of the chromosomal pyrH deletion by means of PCR was chromosomal DNA from the selected ampicillin-resistant, chloramphenicol- and kanamycin-sensitive clones. The thus generated and checked ampicillin-resistant *E. coli* strains with chromosomal pyrH deletion and plasmid-encoded pyrH expression have the designations W3110ΔpyrH/pAF-ts-pyrH and W3110lpp3ΔpyrH/pAF-ts-pyrH.

B) Deletion of the plsC Gene

Analogously to the pyrH gene, the gene plsC, which codes for the enzyme 1-acylglycerol-3-phosphate O-acyltransferase (PlsC) in *E. coli*, was deleted in the *E. coli* strains W3110/pAF-ts-plsC and W3110lpp3/pAF-is-plsC (Datsenko and Wanner, 2000, P.N.A.S. 97: 6640-6645). A DNA fragment coding for the kanamycin resistance marker gene (kanR) was amplified using the primers plsC-fw (SEQ ID No. 13) and plsC-rev (SEQ ID No. 14). The primer plsC-fw codes for a sequence consisting of 30 nucleotides that is homologous to the 5'-end of the plsC gene and a sequence comprising 20 nucleotides that is complementary to a DNA sequence encoding one of the two FRT sites (FLP recognition target) on the plasmid pKD13 (*Coli* Genetic Stock Center (CGSC) No. 7633). The primer plsC-rev codes for a sequence consisting of 30 nucleotides that is homologous to the 3'-end of the plsC gene and a sequence comprising 20 nucleotides that is complementary to a DNA sequence encoding the second FRT site on the plasmid pKD13.

The amplified PCR product was introduced by means of electroporation into the *E. coli* strains W3110/pAF-ts-plsC and W3110lpp3/pAF-ts-plsC (see Example 3). The removal of the chromosomally introduced kanamycin resistance marker gene (kanR) was again done using the enzyme FLP recombinase (encoded on plasmid pCP20). The selection for pCP20-containing cells was also done here on LB agar plates containing 100 mg/l ampicillin (selection for pAF-ts-plsC) and 34 mg/l chloramphenicol (selection for pCP20). A first selection for loss of the temperature-sensitive plasmid pCP20 with simultaneous maintenance of the temperature-sensitive plasmid pAF-ts-plsC was done on LB agar plates containing 100 mg/l ampicillin (selection for pAF-ts-plsC). Later on, the preselected ampicillin-resistant bacteria clones were checked for kanamycin sensitivity, i.e., the loss of the chromosomally introduced kanamycin marker gene, and for chloramphenicol sensitivity, i.e., the loss of the temperature-sensitive plasmid pCP20.

These clones were finally checked for the chromosomal deletion of the plsC gene using the primers plsC-check-for (SEQ ID No. 15) and plsC-check-rev (SEQ ID No. 16). The template used for the checking of the chromosomal plsC deletion by means of PCR was chromosomal DNA from the selected ampicillin-resistant, chloramphenicol- and kanamycin-sensitive clones.

The thus generated and checked ampicillin-resistant *E. coli* strains with chromosomal plsC deletion and plasmid-encoded plsC expression have the designations W3110ΔplsC/pAF-ts-plsC and W3110lpp3ΔplsC/pAF-ts-plsC.

Example 5: Generation of a Production Plasmid Containing Antibiotic Resistance Gene for the Production of Cysteine The starting plasmids used for the cloning and expression of the genes cysEX (codes for feedback-resistant variants of serine acyltransferase; CysE) and orf306 (codes for O-acetylserine/cysteine exporter; EamA) were the base plasmid pMT1 and the production plasmid pACYC184-LH-cysEX-orf306 described in EP0885962B1.

pMT1 contains not only the tetracycline resistance gene (tetR), but also the tac promoter, which is repressed by the LacIq gene product, the gene of which is likewise present on the plasmid, and which can be turned on by an inducer such as, for example, D-lactose or isopropyl-β-D-thiogalactopyranoside (IPTG). A restriction and function map of plasmid pMT1 is shown in FIG. 4. The sequence of the plasmid pMT1 is deposited in the sequence listing (SEQ ID No. 17).

For the generation of a new production plasmid for the production of cysteine, based on pMT1, a NcoI-BsaBI fragment from the plasmid pACYC184-LH-cysEX-orf306 (described in EP0885962 B1), which codes for the genes cysEX and orf306, was ligated with a 2458 bp NcoI-PvuII fragment (codes for ColE1 ori and tetracycline resistance, tetR) from the plasmid pMT1. The ligation preparation was transformed into "DH5α™-T1R *E. coli* cells" (Life Technologies GmbH), multiplied in said cells, and the DNA sequence of the isolated plasmids was verified by means of sequencing. The resulting expression plasmid has the designation pcysEX-GAPDH-ORF306_tetR (see FIG. 5).

Example 6: Generation of a Production Plasmid Containing Antibiotic Resistance Gene for the Production of α-CGTase The starting plasmids used for the cloning and expression of the cyclodextrin glycosyltransferase (CGTase) gene from *Klebsiella pneumoniae* M5a1 (Genebank No. M15264) were again the plasmid pMT1 and the plasmid pCGT described in US2008076158 A1.

For the generation of a new production plasmid for the production of CGTase, based on pMT1, a MauBI-BsaI fragment from the plasmid pCGT, which codes for the CGTase gene from *Klebsiella pneumoniae* M5a1, was ligated with a 4004 bp MauBI-BsaI fragment from the plasmid pMT1. Said 4004 bp fragment from the plasmid pMT1 codes for the ColE1 ori, the lac/tac operator and the tetracyline resistance gene (tetR).

The ligation preparation was transformed into "DH5α™-T1R *E. coli* cells" (Life Technologies GmbH), multiplied in said cells, and the DNA sequence of the isolated plasmids was verified by means of sequencing. The resulting expression plasmid has the designation pCGT_tetR (see FIG. 6).

Example 7: Generation of a Production Plasmid Containing Antibiotic Resistance Gene for the Production of Fab-Anti-Lysozyme The starting plasmids used for the cloning and expression of the genes for the anti-lysozyme Fab fragment were again the plasmid pMT1 and the pFab-anti-lysozyme described in US20080076158 A1.

For the generation of a new production plasmid for the production of the antibody fragment Fab-anti-lysozyme, based on pMT1, a MauBI-BsaI fragment from the plasmid Fab-anti-lysozyme, which codes for the two chains, i.e., the heavy chain ($V_H$-$C_H$1 domains) and the light chain ($V_L$-$C_L$ domains) of the anti-lysozyme Fab fragment, was ligated with a 4004 bp MauBI-BsaI fragment from the plasmid pMT1. Said 4004 bp fragment from the plasmid pMT1 codes for the ColE1 ori, the lac/tac operator and the tetracyline resistance gene (tetR).

The ligation preparation was transformed into "DH5α™-T1R *E. coli* cells" (Life Technologies GmbH), multiplied in said cells, and the DNA sequence of the isolated plasmids was verified by means of sequencing. The resulting expression plasmid has the designation pFab-anti-Lysozyme_tetR (see FIG. 7).

Example 8: Generation of Production Plasmids Containing the Marker Gene pyrH or plsC as Basis for the Creation of Production Plasmids According to the Invention without Antibiotic Resistance Gene The starting plasmids used for the generation of production plasmids containing pyrH or plsC as marker gene were the plasmids pcysEX-GAPDH-ORF306_tetR, pCGT_tetR and pFab-anti-Lysozyme_tetR, as described in Examples 5 to 7. All these plasmids have an individual NcoI restriction site (see FIGS. 5 to 7). This universal NcoI restriction site was used for the cloning or integration of the genes pyrH or plsC.

For this purpose, the PCR products described in Example 1 and cut using the restriction enzyme NcoI were ligated with the plasmids pcysEX-GAPDH-ORF306_tetR, pCGT_tetR and pFab-anti-Lysozyme_tetR, after they were likewise cut using NcoI. The individual ligation preparations were transformed into "DH5α™-T1R *E. coli* cells" (Life Technologies GmbH), multiplied in said cells, and the DNA sequence of the isolated plasmids was verified by means of sequencing. The resulting constructs have, depending on the orientation and on the marker gene used, the following designations:

pcysEX-GAPDH-ORF306_pyrH1_tetR (see FIG. 8) and pcysEX-GAPDH-ORF306_pyrH2_tetR
pCGT_pyrH1_tetR (see FIG. 9) and pCGT_pyrH2_tetR
pFab-anti-Lysozyme_pyrH1_tetR (see FIG. 10) and pFab-anti-Lysozyme_pyrH2_tetR
pcysEX-GAPDH-ORF306_plsC1_tetR (see FIG. 11) and pcysEX-GAPDH-ORF306_plsC2_tetR
pCGT_plsC1_tetR (see FIG. 12) and pCGT_plsC2_tetR
pFab-anti-Lysozyme_plsC1_tetR (see FIG. 13) and pFab-anti-Lysozyme_plsC2_tetR For the final removal of the tetR gene, the procedure was continued with the variants pcysEX-GAPDH-ORF306_pyrH1_tetR, pCGT_pyrH1_tetR, pFab-anti-Lysozyme_pyrH1_tetR, pcysEX-GAPDH-ORF306_plsC1_tetR, pCGT_plsC1_tetR and pFab-anti-Lysozyme_plsC1_tetR (see FIGS. 8 to 13).

Example 9: Removal of the Antibiotic Resistance Gene tetR and Transformation of the Production Plasmids Containing pyrH or plsC as Remaining Marker Gene into *E. coli* Strains with Chromosomal pyrH or plsC Deletion The starting plasmids used for the generation of production plasmids without the antibiotic resistance gene tetR and containing pyrH or plsC as marker gene were the plasmids pcysEX-GAPDH-ORF306_pyrH1_tetR, pCGT_pyrH1_tetR, pFab-anti-Lysozyme_pyrH1_tetR, pcysEX-GAPDH-ORF306_plsC1_tetR, pCGT plsC1_tetR and pFab-anti-Lysozyme_plsC1_tetR, as described in Example 8. The removal of the antibiotic resistance gene tetR from the plasmids pFab-anti-Lysozyme_pyrH1_tetR and pFab-anti-Lysozyme_plsC1_tetR, as described in Example 8, was achieved via a digestion using the restriction enzyme ClaI and subsequent religation.

For the plasmids pcysEX-GAPDH-ORF306_pyrH1_tetR and pcysEX-GAPDH-ORF306_plsC1_tetR, a similar procedure was carried out, except that the gene tetR was removed via a partial digestion using ClaI, since two further ClaI restriction sites are situated in the structural genes cysEX and orf306 (see FIGS. 8 and 11).

In the case of pCGT_plsC1_tetR, the tetR gene was removed from the plasmid via a digestion using the enzymes StuI (cuts to leave blunt end) and FspI (cuts to leave blunt end). In the case of pCGT_pyrH1_tetR, the tetR gene was likewise removed via a partial digestion using the enzymes StuI (cuts to leave blunt end) and FspI (cuts to leave blunt end), since a further FspI restriction site is situated in the pyrH gene (see FIG. 9).

After the restriction digest, the respective linear vector fragments without tetR were purified via an agarose gel electrophoresis and isolated from the agarose gel using the "QIAquick Gel Extraction Kit" (Qiagen GmbH, Hilden, Germany) according to the information from the manufacturer. Thereafter, the tetR-free vector fragment in question was religated. Using a modified $CaCl_2$ method, the corresponding ligation preparations were transformed into the strains W3110ΔpyrH/pAF-ts-pyrH and W3110lpp3ΔpyrH/pAF-ts-pyrH or W3110ΔpyrH/pAF-ts-plsC and W3110lpp3ΔpyrH/pAF-ts-plsC, which strains are described in Example 4. For the transformation, i.e., the introduction of the antibiotic resistance-free production plasmids containing pyrH or plsC as marker gene into *E. coli* strains with corresponding chromosomal deletion (pyrH or plsC), the following procedure was carried out:

After the addition of 5 to 20 µl of the ligation preparation in question to 100 µl of $CaCl_2$-competent cells of the strains W3110ΔpyrH/pAF-ts-pyrH and W3110lpp3ΔpyrH/pAF-ts-pyrH or W3110ΔplsC/pAF-is-plsC and W3110lpp3ΔplsC/pAF-ts-plsC, the cells were incubated on ice for a further 30 minutes. After a brief heat shock at 42° C. for 45 seconds, the cells were cooled on ice for 2 min. Thereafter, 900 µl of LB medium were added to the transformation preparation, and the cells were incubated/regenerated, not at 37° C. as customary, but at 47° C. to 55° C. for 30 to 90 min. The further incubation at elevated nonpermissive temperature was then carried out on LB agar plates or in liquid LB medium without antibiotic (e.g., without tetracycline) at 40-45° C. for 15 to 24 h.

The 30-90 minute regeneration phase at 47° C. to 55° C. and the cultivation for 15 to 24 h at elevated, nonpermissive temperature facilitates the exchange of the temperature-sensitive plasmids pAF-ts-pyrH or pAF-ts-plsC for the final, antibiotic resistance-free production plasmid containing pyrH or plsC as new selection marker gene.

The best transformation results were achieved when the transformed cells were regenerated at 52° C. for 60 min and then incubated on LB agar plates at 42° C. for 20 h.

A preliminary selection for loss of the temperature-sensitive plasmid pAF-ts-pyrH or pAF-ts-plsC with simultaneous exchange for the respective pyrH- or plsC-containing production plasmid without tetracycline resistance gene tetR was done first of all on LB agar plates without antibiotic.

Thereafter, the preselected bacteria clones were checked for ampicillin sensitivity, i.e., the loss of the temperature-sensitive plasmid pAF-ts-pyrH or pAF-ts-plsC.

The pyrH- or plsC-coding production plasmids from ampicillin-sensitive clones were finally checked by means of restriction digest. Restriction maps of the pyrH-coding production plasmids pcysEX-GAPDH-ORF306_pyrH, pCGT_pyrH and pFab-anti-Lysozyme_pyrH, each without the antibiotic resistance gene tetR, are depicted in FIGS. 14 to 16. Restriction maps of the plsC-coding production plasmids pcysEX-GAPDH-ORF306_plsC, pCGT_plsC and pFab-anti-Lysozyme_plsC, each without the antibiotic resistance gene tetR, are depicted in FIGS. 17 to 19.

The thus generated and checked antibiotic resistance-free E. coli strains containing pyrH- or plsC-coding production plasmid and with chromosomal pyrH or plsC deletion have the designations:

W3110ΔpyrH/pcysEX-GAPDH-ORF306_pyrH
W3110lpp3ΔpyrH/pCGT_pyrH
W3110lpp3ΔpyrH/pFab-anti-Lysozyme_pyrH
W3110ΔplsC/pcysEX-GAPDH-ORF306_plsC
W3110lpp3ΔplsC/pCGT_plsC
W3110lpp3ΔplsC/pFab-anti-Lysozyme_plsC Example 10: Cysteine Fermentation Preliminary Culture 1:

In an Erlenmeyer flask (100 ml), 20 ml of LB medium were inoculated with the particular E. coli strain W3110/pcysEX-GAPDH-ORF306_tetR, W3110ΔpyrH/pcysEX-GAPDH-ORF306_pyrH or W3110ΔplsC/pcysEX-GAPDH-ORF306plsC and incubated on a shaker (150 rpm, 30° C.) for seven hours. For a cultivation of construct W3110/pcysEX-GAPDH-ORF306_tetR in the context of the prior art, i.e., with antibiotic as selection agent, the medium was supplemented with 15 mg/L tetracycline.

Preliminary Culture 2:

Thereafter, the preliminary culture 1 was transferred in full to 100 ml of SM1 medium (12 g/l $K_2HPO_4$, 3 g/l $KH_2PO_4$, 5 g/l $(NH_4)_2SO_4$, 0.3 g/l $MgSO_4 \times 7H_2O$, 0.015 g/l $CaCl_2 \times 2H_2O$, 0.002 g/l $FeSO_4 \times 7H_2O$, 1 g/l $Na_3$ citrate× $2H_2O$, 0.1 g/l NaCl, 1 ml/l trace element solution, consisting of 0.15 g/l $Na_2MoO_4 \times 2H_2O$, 2.5 g/l $H_3BO_3$, 0.7 g/l $CoCl_2 \times 6H_2O$, 0.25 g/l $CuSO_4 \times 5H_2O$, 1.6 g/l $MnCl_2 \times 4H_2O$, 0.3 g/l $ZnSO_4 \times 7H_2O$), which was supplemented with 5 g/l glucose and 5 mg/l vitamin B1. The cultures were shaken in Erlenmeyer flasks (1 l) at 30° C. for 17 h at 150 rpm. After this incubation, the optical density at 600 nm ($OD_{600}$) was between 3 and 5. For the cultivation of W3110/pcysEX-GAPDH-ORF306_tetR in the context of the prior art, i.e., with antibiotic as selection agent, the medium was supplemented with 15 mg/L tetracycline.

Main Culture:

The fermentation was carried out in fermenters, BIOSTAT B model, from Sartorius Stedim. A culture vessel with 2 l total volume was used. The fermentation medium (900 ml) contains 15 g/l glucose, 10 g/l tryptone (Difco), 5 g/l yeast extract (Difco), 5 g/l $(NH_4)_2SO_4$, 1.5 g/l $KH_2PO_4$, 0.5 g/l NaCl, 0.3 g/l $MgSO_4 \times 7H_2O$, 0.015 g/l $CaCl_2 \times 2H_2O$, 0.075 g/l $FeSO_4 \times 7H_2O$, 1 g/l $Na_3$ citrate× $2H_2O$ and 1 ml of trace element solution (see above) and 0.005 g/l vitamin B1. The pH in the fermenter was initially adjusted to 6.5 by pumping in a 25% $NH_4OH$ solution.

During the fermentation, the pH was maintained by automatic correction at a level of 6.5 using 25% $NH_4OH$. For the inoculation, 100 ml of the preliminary culture 2 were pumped into the fermenter vessel. The starting volume was therefore about 1 l. The cultures were initially stirred at 400 rpm and aerated with 2 vvm of a compressed air sterilized via a sterile filter. Under these starting conditions, the oxygen probe had been calibrated to 100% saturation prior to the inoculation. The nominal value for the $O_2$ saturation during the fermentation was set to 50%. After the $O_2$ saturation fell below the nominal value, a regulation cascade was started in order to bring the $O_2$ saturation back to the nominal value. In this connection, the gas supply was first continuously increased (to max. 5 vvm) and then the stirring rate was continuously raised (to max. 1500 rpm).

The fermentation was carried out at a temperature of 30° C. After a fermentation time of 2 h, a sulfur source was fed in in the form of a sterile 60% sodium thiosulfate×5$H_2O$ stock solution at a rate of 1.5 ml per hour. Once the glucose content in the fermenter of initially 15 g/l had dropped to approximately 2 g/l, a 56% glucose solution was continuously metered in. The feeding rate was set such that the glucose concentration in the fermenter, from then on, no longer exceeded 2 g/l.

Glucose was determined using a glucose analyzer from YSI (Yellow Springs, Ohio, USA). For the fermentation of construct W3110/pcysEX-GAPDH-ORF306 tetR in the context of the prior art, i.e., with antibiotic as selection agent, the medium was supplemented with 15 mg/L tetracycline.

The fermentation period was 48 hours. Thereafter, samples were collected and the content of L-cysteine and the derivatives derived therefrom in the culture supernatant (especially L-cysteine and thiazolidine) and in the precipitate (L-cystine) were determined separately from one another. For this purpose, the colorimetric assay by Gaitonde (Gaitonde, M. K. (1967), Biochem. J. 104, 627-633) was used in each case. The L-cystine present in the precipitate first had to be dissolved in 8% hydrochloric acid before it could be quantified in the same way. The values listed in Table 1 for total cysteine correspond to the sum of the L-cysteine in the culture supernatant and L-cystine in the precipitate. In this connection, each molecule of L-cystine corresponds to two molecules of L-cysteine.

TABLE 1

Content of total cysteine (L-cysteine$_{culture\ supernatant}$ + L-cystine$_{precipitate}$) in the culture broth after 48 h and stability of the production plasmids

| Strain | Total cysteine (g/L) | Plasmid stability |
|---|---|---|
| W3110/pcysEX-GAPDH-ORF306_tet$^R$ (cultivated with tetracycline)* | 19.0 ± 0.4 | 95% ± 5% |

TABLE 1-continued

Content of total cysteine (L-cysteine$_{culture\ supernatant}$ + L-cystine$_{precipitate}$) in the culture broth after 48 h and stability of the production plasmids

| Strain | Total cysteine (g/L) | Plasmid stability |
|---|---|---|
| W3110/pcysEX-GAPDH-ORF306_tet$^R$ (cultivated without tetracycline) | 10.0 ± 4.1 | 60% ± 19% |
| W3110ΔpyrH × pcysEX-GAPDH-ORF306 pyrH1** | 20.4 ± 0.3 | 97% ± 3% |
| W3110ΔplsC/pcysEX-GAPDH-ORF306_plsC** | 21.1 + 0.3 | 95% ± 5% |

*Construct in the context of the prior art (comparative example)
**Construct according to the invention

Example 11: Secretory Production of a Cyclodextrin Glycosyltransferase on the 10 l Scale (Fermentation)

With the aid of an lpp mutant of E. coli, biotechnologically relevant enzymes such as, for example, CGTases can be produced and secreted into the medium (US2008076158 A1).

The secretory production of the CGTase was carried out in 10 L stirred tank fermenters using the strains W3110lpp3/pCGT_tetR (control), W3110lpp3ΔpyrH/pCGT_pyrH and W3110lpp3ΔpyrH/pCGT_plsC.

The fermenter filled with 6 l of the fermentation medium FM4 (1.5 g/l KH$_2$PO$_4$; 5 g/l (NH$_4$)$_2$SO$_4$; 0.5 g/l MgSO$_4$×7H$_2$O; 0.15 g/l CaCl$_2$×2H$_2$O, 0.075 g/l FeSO$_4$×7H$_2$O; 1 g/l Na$_3$ citrate×2H$_2$O; 0.5 g/l NaCl; 1 ml/l trace element solution (0.15 g/l Na$_2$MoO$_4$×2H$_2$O; 2.5 g/l Na$_3$BO$_3$; 0.7 g/l CoCl$_2$×6H$_2$O; 0.25 g/l CuSO$_4$×5H$_2$O; 1.6 g/l MnCl$_2$×4H$_2$O; 0.3 g/l ZnSO$_4$×7H$_2$O); 5 mg/l vitamin B$_1$; 3 g/l Phytone; 1.5 g/l yeast extract; 10 g/l glucose) was inoculated in the ratio of 1:10 with a preliminary culture, which was cultivated overnight in the same medium. During the fermentation, a temperature of 30° C. was set and the pH was maintained constantly at a level of 7.0 by metering in NH$_4$OH or H$_3$PO$_4$. Glucose was metered in throughout the fermentation, with a maximum glucose concentration in the fermentation medium of <10 g/l being striven for. Expression was induced by addition of isopropyl-β-D-thiogalactopyranoside (IPTG) to 0.1 mM at the end of the logarithmic growth phase.

For the fermentation of the construct W3110lpp3/pCGT_tetR in the context of the prior art, i.e., with antibiotic as selection agent, the medium was supplemented with 15 mg/L tetracycline.

After 72 h of fermentation, samples were collected, the cells were removed from the fermentation medium by centrifugation and the CGTase content in the fermentation supernatant was determined, as described in Example 4 of US2008076158A1.

Table 2 lists the yields of functional CGTase and also the activities in the fermentation supernatant.

TABLE 2

Cyclodextrin glycosyltransferase yields in the fermentation supernatant after 72 hours of fermentation

| Strain | CGTase (U/ml) | CGTase (mg/l) | Plasmid stability |
|---|---|---|---|
| W3110lpp3/pCGT_tetR (cultivated with tetracycline)* | 555 ± 15 | 3750 ± 145 | 97% ± 3% |
| W3110lpp3/pCGT_tetR (cultivated without tetracycline) | 340 ± 65 | 2210 ± 425 | 55% ± 21% |
| W3110lpp3ΔpyrH/pCGT_pyrH** | 560 ± 25 | 3795 ± 160 | 98% ± 2% |
| W3110lpp3ΔplsC/pCGT_plsC** | 570 ± 30 | 3810 ± 190 | 98% ± 2% |

*Construct in the context of the prior art (comparative example)
**Construct according to the invention

Example 12: Secretory, Fermentative Production of the Fab Antibody Fragment Anti-Lysozyme-Fab on the 10 l Scale With the aid of an lpp mutant of E. coli, functional Fab antibody fragments can also be produced extracellularly (US2008076158A1). In this case, the cell must simultaneously synthesize the corresponding fragments of the light chain, which comprises the domains V$_L$ and C$_L$, and of the heavy chain, which comprises the domains V$_H$ and CH1, and then secrete them into the periplasm and ultimately into the fermentation medium. Outside the cytoplasm, the two chains then assemble to form the functional Fab fragment.

The present example describes the production of a Fab fragment of the well characterized anti-lysozyme antibody D1.3. The plasmids pFab-anti-Lysozyme_tetR, pFab-anti-Lysozyme_pyrH and pFab-anti-Lysozyme_plsC contain not only the marker genes tetR, pyrH and plsC, respectively, but also, inter alia, the structural genes for the HC and the LC of the Fab fragment in the form of an operon. In this case, the HC is fused in frame to the 3'-end of the ompA signal sequence (ompA$^{SS}$) and the LC is fused in frame to the 3'-end of a CGTase signal sequence (cgt$^{SS}$). The expression of the ompA$^{SS}$-HC-cgt$^{SS}$-LC operon is under the control of the tac promoter.

The production of the anti-lysozyme Fab fragment on the 10 l scale was carried out analogously to the method described in Example 11 on the basis of CGTase, using the strains W3110lpp3/pFab-anti-Lysozyme_tetR, W3110lpp3ΔpyrH/pFab-anti-Lysozyme_pyrH and W3110lpp3ΔplsC/pFab-anti-Lysozyme_plsC. For the fermentation of E. coli W3110lpp3/pFab-anti-Lysozyme_tetR in the context of the prior art, i.e., with antibiotic as selection agent, the medium was supplemented with 15 mg/L tetracycline.

After 72 h of fermentation, samples were collected and then the cells were removed from the fermentation medium by centrifugation.

The anti-lysozyme Fab fragment was purified from the fermentation supernatants by means of affinity chromatography, as described in Skerra (1994, Gene 141, 79-84).

The purified anti-lysozyme Fab fragment was quantified and its activity determined via an ELISA assay with lysozyme as antigen (Skerra, 1994, Gene 141, 79-84).

Table 2 lists the projected yields of functional anti-lysozyme Fab fragment in the fermentation supernatant, on the basis of isolated amounts of, in each case, 20 ml of fermentation supernatant after 72 h of fermentation.

TABLE 3

Anti-lysozyme Fab fragment yields in the fermentation supernatant after 72 h of fermentation

| Strain | Anti-lysozyme Fab fragment yields [mg/l] in the fermentation supernatant (projected) | Plasmid stability |
|---|---|---|
| W3110lpp3/pFab-anti-Lysozyme_tetR (cultivated with tetracycline)* | 1440 ± 110 | 97% ± 3% |
| W3110lpp3/pFab-anti-Lysozyme_tetR (cultivated without tetracycline) | 625 ± 250 | 55% ± 20% |
| W3110lpp3ΔpyrH/pFab-anti-Lysozyme_pyrH** | 1580 ± 115 | 98% ± 2% |
| W3110lpp3ΔplsC/pFab-anti-Lysozyme_plsC** | 1610 ± 130 | 98% ± 2% |

*Construct in the context of the prior art (comparative example)
**Construct according to the invention Example 13: Determination of Plasmid Stability Plasmid stability was checked by means of plasmid preparation with subsequent restriction digest. For this purpose, completion of the cultivation of the production strains (e.g., after 72 h of fermentation) was followed by plating out various dilutions of the cultures on LB agar plates. For the subsequent ascertainment of plasmid stability, i.e., the identification of plasmid-bearing cells (colonies), only LB plates with individual colonies were used for the evaluation.

Altogether, 50 individual colonies were cultivated in liquid LB medium for 15 to 20 hours and then plasmid DNA was isolated from said cultures. Characteristic restriction patterns for the individual production plasmids were used as a basis to verify the correctness of the isolated plasmids.

The invention claimed is:

1. A microorganism strain for producing low-molecular-weight substances or proteins, said microorganism strain comprising: (a) a genome containing a mutation in a gene, which mutation brings about an auxotrophy in the microorganism strain, and (b) a production plasmid encoding at least one enzyme for producing a low-molecular-weight substance or at least one recombinant protein and also a functional copy of the gene, the chromosomal inactivation of which brings about the auxotrophy, wherein the auxotrophy is a nonfeedable auxotrophy and the gene is a pyrH gene or a plsC gene or homologous genes thereof.

2. The microorganism strain as claimed in claim 1, wherein the mutation of the gene brings about the nonfeedable auxotrophy in the strain, and leads to inactivation of said gene.

3. The microorganism strain as claimed in claim 1, wherein the mutation of the gene brings about the nonfeedable auxotrophy in the strain, and leads to inactivation of an activity of a gene product coded by the gene.

4. A method for producing a strain as claimed in claim 1, comprising: (i) introducing into said strain a temperature-sensitive plasmid comprising a functional copy of a pyrH gene or a functional copy of a plsC gene or homologous genes thereof; (ii) mutating or deleting in the genome of the strain the pyrH gene or the plsC gene or homologous genes thereof which leads to a nonfeedable auxotrophy in the strain; (iii) transforming said strain with a production plasmid comprising a gene encoding an enzyme for the production of a low-molecular weight substance or a recombinant protein and also a functional copy of the pyrH gene or a functional copy of the plsC gene or homologous genes thereof; and (iv) exchanging the temperature-sensitive plasmid for the production plasmid at a non-permissive temperature.

5. The method as claimed in claim 4, wherein the temperature-sensitive plasmid has a temperature-sensitive origin of replication.

6. The method as claimed in claim 5, wherein cells are exposed, immediately after the transformation with the production plasmid, to a temperature shock at 47-55° C. for 30-90 min and then further incubation is then carried out at the nonpermissive temperature of 37-45° C.

7. A method for producing low-molecular-weight substances or proteins comprising producing the low-molecular-weight substances or proteins with a microorganism strain as claimed in claim 1 by culturing said strain in an antibiotic-free fermentation medium.

8. A method for producing low-molecular-weight substances or proteins comprising producing the to substances or proteins with a microorganism strain as claimed in claim 1 by culturing said strain in an antibiotic-free fermentation medium.

* * * * *

SEQUENCE LISTING

```
<160> NUMBER OF SEQ ID NOS: 17

<210> SEQ ID NO 1
<211> LENGTH: 726
<212> TYPE: DNA
<213> ORGANISM: Escherichia coli
<220> FEATURE:
<221> NAME/KEY: gene
<222> LOCATION: (1)..(726)
<223> OTHER INFORMATION: pyrH

<400> SEQUENCE: 1
atggctacca atgcaaaacc cgtctataaa cgcattctgc ttaagttgag tggcgaagct      60
ctgcagggca ctgaaggctt cggtattgat gcaagcatac tggatcgtat ggctcaggaa     120
atcaaagaac tggttgaact gggtattcag gttggtgtgg tgattggtgg gggtaacctg     180
ttccgtggcg ctggtctggc gaaagcgggt atgaaccgcg ttgtgggcga ccacatgggg     240
atgctggcga ccgtaatgaa cggcctggca atgcgtgatg cactgcaccg cgcctatgtg     300
aacgctcgtc tgatgtccgc tattccattg aatggcgtgt gcgacagcta cagctgggca     360
gaagctatca gcctgttgcg caacaaccgt gtggtgatcc tctccgccgg tacaggtaac     420
ccgttcttta ccaccgactc agcagcttgc ctgcgtggta tcgaaattga agccgatgtg     480
gtgctgaaag caaccaaagt tgacggcgtg tttaccgctg atccggcgaa agatccaacc     540
gcaaccatgt acgagcaact gacttacagc gaagtgctgg aaaaagagct gaaagtcatg     600
gacctggcgg ccttcacgct ggctcgtgac cataaattac cgattcgtgt tttcaatatg     660
aacaaaccgg gtgcgctgcg ccgtgtggta atgggtgaaa agaagggac tttaatcacg     720 gaataa                                                                726
```

<210> SEQ ID NO 2
<211> LENGTH: 241
<212> TYPE: PRT
<213> ORGANISM: Escherichia coli
<220> FEATURE:
<221> NAME/KEY: PEPTIDE
<222> LOCATION: (1)..(241)

<400> SEQUENCE: 2

Met Ala Thr Asn Ala Lys Pro Val Tyr Lys Arg Ile Leu Leu Lys Leu
1               5                   10                  15

Ser Gly Glu Ala Leu Gln Gly Thr Glu Gly Phe Gly Ile Asp Ala Ser
            20                  25                  30

Ile Leu Asp Arg Met Ala Gln Glu Ile Lys Glu Leu Val Glu Leu Gly
        35                  40                  45

Ile Gln Val Gly Val Val Ile Gly Gly Gly Asn Leu Phe Arg Gly Ala
    50                  55                  60

Gly Leu Ala Lys Ala Gly Met Asn Arg Val Val Gly Asp His Met Gly
65                  70                  75                  80

Met Leu Ala Thr Val Met Asn Gly Leu Ala Met Arg Asp Ala Leu His
                85                  90                  95

Arg Ala Tyr Val Asn Ala Arg Leu Met Ser Ala Ile Pro Leu Asn Gly
            100                 105                 110

Val Cys Asp Ser Tyr Ser Trp Ala Glu Ala Ile Ser Leu Leu Arg Asn
        115                 120                 125

Asn Arg Val Val Ile Leu Ser Ala Gly Thr Gly Asn Pro Phe Phe Thr
    130                 135                 140

Thr Asp Ser Ala Ala Cys Leu Arg Gly Ile Glu Ile Glu Ala Asp Val
145                 150                 155                 160

Val Leu Lys Ala Thr Lys Val Asp Gly Val Phe Thr Ala Asp Pro Ala
                165                 170                 175

Lys Asp Pro Thr Ala Thr Met Tyr Glu Gln Leu Thr Tyr Ser Glu Val
            180                 185                 190

Leu Glu Lys Glu Leu Lys Val Met Asp Leu Ala Ala Phe Thr Leu Ala
        195                 200                 205

Arg Asp His Lys Leu Pro Ile Arg Val Phe Asn Met Asn Lys Pro Gly
    210                 215                 220

Ala Leu Arg Arg Val Val Met Gly Glu Lys Glu Gly Thr Leu Ile Thr
225                 230                 235                 240

Glu

<210> SEQ ID NO 3
<211> LENGTH: 738
<212> TYPE: DNA
<213> ORGANISM: Escherichia coli
<220> FEATURE:
<221> NAME/KEY: gene
<222> LOCATION: (1)..(738)
<223> OTHER INFORMATION: plsC

<400> SEQUENCE: 3
atgctatata tctttcgtct tattattacc gtgatttaca gcatcttagt ctgtgtattc      60
ggctccattt actgcctttt cagcccgcgt aacccgaaac atgtggccac ctttgggcat     120
atgtttggcc gtcttgcgcc gctgtttggc ctgaaagttg agtgccgtaa acctacagac     180
gctgaaagct acggcaatgc tatctatatc gctaaccacc agaacaacta tgacatggtg     240
acagcatcga acatcgtgca accgccgacg gtgacggtag gtaaaaagag cttgctgtgg     300

-continued

```
atcccttct tcgggcagtt gtactggtta accggcaact tattgatcga cagaaacaat    360
cgcactaaag ctcacggcac cattgcggaa gtagtgaatc acttcaaaaa acgccgtatt    420
tccatctgga tgttcccgga aggaacccgc agccgtggtc gcggcctgct accgttcaag    480
actggagcat tcacgcggc aattgcggcg ggcgtcccga ttattcccgt gtgcgtctct    540
acaacttcga ataagattaa tcttaatcga ctgcacaacg gtctggtgat tgtcgaaatg    600
ctgccgccaa ttgacgtcag tcagtatggc aaagatcagg ttcgtgagct ggctgcccat    660
tgtcgttcga taatggaaca aaaaatcgcc gagctcgata agaagtcgc agaacgcgaa    720
gccgccggaa aagttttaa                                                 738
```

<210> SEQ ID NO 4
<211> LENGTH: 245
<212> TYPE: PRT
<213> ORGANISM: Escherichia coli
<220> FEATURE:
<221> NAME/KEY: PEPTIDE
<222> LOCATION: (1)..(245)
<220> FEATURE:
<221> NAME/KEY: PEPTIDE
<222> LOCATION: (1)..(245)
<223> OTHER INFORMATION: PlsC

<400> SEQUENCE: 4

Met Leu Tyr Ile Phe Arg Leu Ile Ile Thr Val Ile Tyr Ser Ile Leu
1               5                   10                  15

Val Cys Val Phe Gly Ser Ile Tyr Cys Leu Phe Ser Pro Arg Asn Pro
            20                  25                  30

Lys His Val Ala Thr Phe Gly His Met Phe Gly Arg Leu Ala Pro Leu
        35                  40                  45

Phe Gly Leu Lys Val Glu Cys Arg Lys Pro Thr Asp Ala Glu Ser Tyr
    50                  55                  60

Gly Asn Ala Ile Tyr Ile Ala Asn His Gln Asn Asn Tyr Asp Met Val
65                  70                  75                  80

Thr Ala Ser Asn Ile Val Gln Pro Pro Thr Val Thr Val Gly Lys Lys
                85                  90                  95

Ser Leu Leu Trp Ile Pro Phe Phe Gly Gln Leu Tyr Trp Leu Thr Gly
            100                 105                 110

Asn Leu Leu Ile Asp Arg Asn Asn Arg Thr Lys Ala His Gly Thr Ile
        115                 120                 125

Ala Glu Val Val Asn His Phe Lys Lys Arg Arg Ile Ser Ile Trp Met
    130                 135                 140

Phe Pro Glu Gly Thr Arg Ser Arg Gly Arg Gly Leu Leu Pro Phe Lys
145                 150                 155                 160

Thr Gly Ala Phe His Ala Ala Ile Ala Ala Gly Val Pro Ile Ile Pro
                165                 170                 175

Val Cys Val Ser Thr Thr Ser Asn Lys Ile Asn Leu Asn Arg Leu His
            180                 185                 190

Asn Gly Leu Val Ile Val Glu Met Leu Pro Pro Ile Asp Val Ser Gln
        195                 200                 205

Tyr Gly Lys Asp Gln Val Arg Glu Leu Ala Ala His Cys Arg Ser Ile
    210                 215                 220

Met Glu Gln Lys Ile Ala Glu Leu Asp Lys Glu Val Ala Glu Arg Glu
225                 230                 235                 240

Ala Ala Gly Lys Val
            245

```
<210> SEQ ID NO 5
<211> LENGTH: 40
<212> TYPE: DNA
<213> ORGANISM: Artificial Sequence
<220> FEATURE:
<223> OTHER INFORMATION: synthetic oligonucleotide pyrH-NcoI-fw (for
      amplification of pyrH gene with native promoter)

<400> SEQUENCE: 5 cccccccatgg ccatcttgta aattcagcta acccttgtgg                            40

<210> SEQ ID NO 6
<211> LENGTH: 40
<212> TYPE: DNA
<213> ORGANISM: Artificial Sequence
<220> FEATURE:
<223> OTHER INFORMATION: synthetic oligonucleotide pyrH-NcoI-rev (for
      amplification of pyrH gene with native promoter)

<400> SEQUENCE: 6
ggggccatgg atcctcacgt acttttgtac gctccggttg                             40

<210> SEQ ID NO 7
<211> LENGTH: 37
<212> TYPE: DNA
<213> ORGANISM: Artificial Sequence
<220> FEATURE:
<223> OTHER INFORMATION: synthetic oligonucleotide plsC-NcoI-fw (for
      amplification of plsC gene with native promoter)

<400> SEQUENCE: 7
ccccccatgg atttgctcca tgtaaaactg gctaaag                                37

<210> SEQ ID NO 8
<211> LENGTH: 40
<212> TYPE: DNA
<213> ORGANISM: Artificial Sequence
<220> FEATURE:
<223> OTHER INFORMATION: synthetic oligonucleotide plsC-NcoI-rev (for
      amplification of plsC gene with native promoter)

<400> SEQUENCE: 8
ggggccatgg tgaaaccgtt gtttattcat gcgttgcgat                             40

<210> SEQ ID NO 9
<211> LENGTH: 71
<212> TYPE: DNA
<213> ORGANISM: Artificial Sequence
<220> FEATURE:
<223> OTHER INFORMATION: synthetic oligonucleotide pyrH-fw (for deletion
      of genomic pyrH gene)

<400> SEQUENCE: 9
cagtcttaat tatcaaaaag gagccgcctg agggcggctt cttttgtgc cgtgtaggct         60 ggagctgctt c                                                            71

<210> SEQ ID NO 10
<211> LENGTH: 70
<212> TYPE: DNA
<213> ORGANISM: Artificial Sequence
<220> FEATURE:
<223> OTHER INFORMATION: synthetic oligonucleotide pyrH-rev (for
      deletion of genomic pyrH gene)
```

<400> SEQUENCE: 10
gtaatcgtct ggattattag gctattttat ttgccatttt ggccccgggc atgggaatta    60
gccatggtcc    70

<210> SEQ ID NO 11
<211> LENGTH: 30
<212> TYPE: DNA
<213> ORGANISM: Artificial Sequence
<220> FEATURE:
<223> OTHER INFORMATION: synthetic oligonucleotide pyrH-check-for (for
      verification of genomic pyrH deletion)

<400> SEQUENCE: 11
gcataacgct gaagtgactg gcttcatccg    30

<210> SEQ ID NO 12
<211> LENGTH: 30
<212> TYPE: DNA
<213> ORGANISM: Artificial Sequence
<220> FEATURE:
<223> OTHER INFORMATION: synthetic oligonucleotide pyrH-check-rev (for
      verification of genomic pyrH deletion)

<400> SEQUENCE: 12
cagaccagac agtcacacac agtggaagtg    30

<210> SEQ ID NO 13
<211> LENGTH: 71
<212> TYPE: DNA
<213> ORGANISM: Artificial Sequence
<220> FEATURE:
<223> OTHER INFORMATION: synthetic oligonucleotide plsC-fw (for deletion
      of genomic plsC gene)

<400> SEQUENCE: 13
ctgacgtcaa ttggcggcag catttcgaca atcaccagac cgttgtgcag cgtgtaggct    60
ggagctgctt c    71

<210> SEQ ID NO 14
<211> LENGTH: 71
<212> TYPE: DNA
<213> ORGANISM: Artificial Sequence
<220> FEATURE:
<223> OTHER INFORMATION: synthetic oligonucleotide plsC-rev (for
      deletion of genomic plsC gene)

<400> SEQUENCE: 14
ctgacgtcaa ttggcggcag catttcgaca atcaccagac cgttgtgcag cgtgtaggct    60
ggagctgctt c    71

<210> SEQ ID NO 15
<211> LENGTH: 30
<212> TYPE: DNA
<213> ORGANISM: Artificial Sequence
<220> FEATURE:
<223> OTHER INFORMATION: synthetic oligonucleotide plsC-check-for (for
      verification of genomic plsC deletion)

<400> SEQUENCE: 15
cgagattcaa gtagcggcgg aacgggtagc    30

```
<210> SEQ ID NO 16
<211> LENGTH: 30
<212> TYPE: DNA
<213> ORGANISM: Artificial Sequence
<220> FEATURE:
<223> OTHER INFORMATION: synthetic oligonucleotide plsC-check-rev (for
      verification of genomic plsC deletion)

<400> SEQUENCE: 16
gttaagtcgt catccggcag cgtattcaac                                        30

<210> SEQ ID NO 17
<211> LENGTH: 4487
<212> TYPE: DNA
<213> ORGANISM: Artificial Sequence
<220> FEATURE:
<223> OTHER INFORMATION: sequence of plasmid pMT1

<400> SEQUENCE: 17
tcgtgtcgct caaggcgcac tcccgttctg gataatgttt tttgcgccga catcataacg       60
gttctggcaa atattctgaa atgagctgtt gacaattaat catcggctcg tataatgtgt      120
ggaattgtga gcggataaca atttcacaca ggaaacagaa ttcccgggga tccgtcgacc      180
tgcagccaag cttggctgtt ttggcggatg agagaagatt ttcagcctga tacagattaa      240
atcagaacgc agaagcggtc tgataaaaca gaatttgcct ggcggcagta gcgcggtggt      300
cccacctgac cccatgccga actcagaagt gaaacgccgt agcgccgatg gtagtgtggg      360
gtctccccat gcgagagtag ggaactgcca ggcatcaaat aaaacgaaag gctcagtcga      420
aagactgggc ctttcgtttt atctgttgtt tgtcggtgaa cgctctcctg agtaggacaa      480
atccgccggg agcggatttg aacgttgcga agcaacggcc cggagggtgg cgggcaggac      540
gcccgccata aactgccagg catcaaatta agcagaaggc catcctgacg gatggccttt      600
ttgcgtttct acaaactctt tgtttatttt tctaaatac attcaaatat gtatccgctc      660
atgagacaat aaccctgata aatgcttcaa taatattgaa aaaggaagag tatgagtatt      720
cggtcgccgc atacactatt ctcagaatga cttggttgag tccatggcgg ccgccgatct      780
aggtgaagat ccttttttgat aatctcatga ccaaaatccc ttaacgtgag ttttcgttcc      840
actgagcgtc agacccgta gaaaagatca aaggatcttc ttgagatcct ttttttctgc      900
gcgtaatctg ctgcttgcaa acaaaaaaac caccgctacc agcggtggtt tgtttgccgg      960
atcaagagct accaactctt tttccgaagg taactggctt cagcagagcg cagataccaa     1020
atactgtcct tctagtgtag ccgtagttag gccaccactt caagaactct gtagcaccgc     1080
ctacatacct cgctctgcta atcctgttac cagtggctgc tgccagtggc gataagtcgt     1140
gtcttaccgg gttggactca agacgatagt taccggataa ggcgcagcgg tcgggctgaa     1200
cggggggttc gtgcacacag cccagcttgg agcgaacgac ctacaccgaa ctgagatacc     1260
tacagcgtga gcattgagaa agcgccacgc ttcccgaagg gagaaaggcg gacaggtatc     1320
cggtaagcgg cagggtcgga acaggagagc gcacgaggga gcttccaggg ggaaacgcct     1380
ggtatcttta tagtcctgtc gggtttcgcc acctctgact tgagcgtcga tttttgtgat     1440
gctcgtcagg gggcggagc ctatggaaaa acgattctca tgtttgacag cttatcatcg     1500
ataagctcca ggacccaacg ctgcccgaga tgcgccgcgt gcggctgctg gagatggcgg     1560
acgcgatgga tatgttctgc caagggttgg tttgcgcatt cacagttctc cgcaagaatt     1620
gattggctcc aattcttgga gtggtgaatc cgttagcgag gtgccgccgg cttccattca     1680
ggtcgaggtg gcccggctcc atgcaccgcg acgcaacgcg gggaggcaga caaggtatag     1740
```

-continued

```
ggcggcgcct acaatccatg ccaacccgtt ccatgtgctc gccgaggcgg cataaatcgc    1800
cgtgacgatc agcggtccaa tgatcgaagt taggctggta agagccgcga gcgatccttg    1860
aagctgtccc tgatggtcgt catctacctg cctggacagc atggcctgca acgcgggcat    1920
cccgatgccg ccggaagcga gaagaatcat aatggggaag gccatccagc ctcgcgtcgc    1980
gaacgccagc aagacgtagc ccagcgcgtc ggccgccatg ccggcgataa tggcctgctt    2040
ctcgccgaaa cgtttggtgg cgggaccagt gacgaaggct tgagcgaggg cgtgcaagat    2100
tccgaatacc gcaagcgaca ggccgatcat cgtcgcgctc cagcgaaagc ggtcctcgcc    2160
gaaaatgacc cagagcgctg ccggcacctg tcctacgagt tgcatgataa agaagacagt    2220
cataagtgcg gcgacgatag tcatgccccg cgccaccgg aaggagctga ctgggttgaa    2280
ggctctcaag gcatcggtc gacgctctcc cttatgcgac tcctgcatta ggaagcagcc    2340
cagtagtagg ttgaggccgt tgagcaccgc cgccgcaagg aatggtgcat gcaaggagat    2400
ggcgcccaac agtccccccgg ccacggggcc tgccaccata cccacgccga aacaagcgct    2460
catgagcccg aagtggcgag cccgatcttc ccatcggtg atgtcggcga tataggcgcc    2520
agcaaccgca cctgtggcgc cggtgatgcc ggccacgatg cgtccggcgt agaggatcca    2580
caggacgggt gtggtcgcca tgatcgcgta gtcgatagtg gctccaagta gcgaagcgag    2640
caggactggg cggcggccaa agcggtcgga cagtgctccg agaacgggtg cgcatagaaa    2700
ttgcatcaac gcatatagcg ctagcagcac gccatagtga ctggcgatgc tgtcggaatg    2760
gacgatatcc cgcaagaggc ccggcagtac cggcataacc aagcctatgc ctacagcatc    2820
cagggtgacg gtgccgagga tgacgatgag cgcattgtta gatttcatac acggtgcctg    2880
actgcgttag caatttaact gtgataaact accgcattaa agcttatcga tgataagctg    2940
tcaaacatgg caggcctccc ccagaagtcg cttgcggtat tcggaatctt gcacgccctc    3000
gctcaagcct tcgtcactgg tcccgccacc aaacgtttcg gcgagaagca ggccattatc    3060
gccggcatgg cggccgacgc gctgggctac gtcttgctgg cgttcgcgaa cgccagcaag    3120
acgtagccca gcgcgtcggc cagcttgcaa ttcgcgctaa cttacattaa ttgcgttgcg    3180
ctcactgccc gctttccagt cgggaaacct gtcgtgccag ctgcattaat gaatcggcca    3240
acgcgcgggg agaggcggtt tgcgtattgg gcgccagggt ggttttcctt ttcaccagtg    3300
agacgggcaa cagctgattg cccttcaccg cctggccctg agagagttgc agcaagcggt    3360
ccacgctggt ttgccccagc aggcgaaaat cctgtttgat ggtggttgac ggcgggatat    3420
aacatgagct gtcttcggta tcgtcgtatc ccactaccga gatatccgca ccaacgcgca    3480
gcccggactc ggtaatggcg cgcattgcgc ccagcgccat ctgatcgttg gcaaccagca    3540
tcgcagtggg aacgatgccc tcattcagca tttgcatggt tgttgaaaa ccggacatgg    3600 cactccagtc gccttccgt tccgctatcg gctgaatttg attgcgagtg agatatttat    3660
gccagccagc cagacgcaga cgcgccgaga cagaacttaa tgggcccgct aacagcgcga    3720
tttgctggtg acccaatgcg accagatgct ccacgcccag tcgcgtaccg tcttcatggg    3780
agaaaataat actgttgatg ggtgtctggt cagagacatc aagaaataac gccggaacat    3840 tagtgcagg agcttccaca gcaatggcat cctggtcatc cagcggatag ttaatgatca    3900
gcccactgac gcgttgcgcg agaagattgt gcaccgccgc tttacaggct tcgacgccgc    3960
ttcgttctac catcgacacc accacgctgg cacccagttg atcggcgcga gatttaatcg    4020
ccgcgacaat ttgcgacggc gcgtgcaggg ccagactgga ggtggcaacg ccaatcagca    4080
acgactgttt gcccgccagt tgttgtgcca cgcggttggg aatgtaattc agctccgcca    4140
```

```
tcgccgcttc cactttttcc cgcgttttcg cagaaacgtg gctggcctgg ttcaccacgc    4200
gggaaacggt ctgataagag acaccggcat actctgcgac atcgtataac gttactggtt    4260
tcacattcac caccctgaat tgactctctt ccgggcgcta tcatgccata ccgcgaaagg    4320
ttttgcacca ttcgatggtg tcaacgtaaa tgcatgccgc ttcgccttcg cgcgcgaatt    4380
gcaagctgat ccgggcttat cgactgcacg gtgcaccaat gcttctggcg tcaggcagcc    4440
atcggaagct gtggtatggc tgtgcaggtc gtaaatcact gcataat                 4487
```